United States Patent
Bolam et al.

(10) Patent No.: US 7,275,540 B2
(45) Date of Patent: Oct. 2, 2007

(54) MRI/NMR-COMPATIBLE, TIDAL VOLUME CONTROL AND MEASUREMENT SYSTEMS, METHODS, AND DEVICES FOR RESPIRATORY AND HYPERPOLARIZED GAS DELIVERY

(75) Inventors: Kenneth Bolam, Raleigh, NC (US); James Borgen, Raleigh, NC (US)

(73) Assignee: Medi-Physics, Inc., Princeton, NJ (US)

( * ) Notice: Subject to any disclaimer, the term of this patent is extended or adjusted under 35 U.S.C. 154(b) by 406 days.

(21) Appl. No.: 10/828,824

(22) Filed: Apr. 21, 2004

(65) Prior Publication Data

US 2004/0230113 A1 Nov. 18, 2004

(51) Int. Cl.
- A61M 16/00 (2006.01)
- A62B 7/00 (2006.01)
- F16K 31/02 (2006.01)
- F16K 11/00 (2006.01)
- G05D 11/02 (2006.01)

(52) U.S. Cl. .......................... 128/204.18; 128/204.21; 128/204.22; 128/204.23; 128/203.25

(58) Field of Classification Search ................ 600/411, 600/413, 428; 128/204.18, 204.21–204.23, 128/203.11, 203.14
See application file for complete search history.

(56) References Cited

U.S. PATENT DOCUMENTS

| | | |
|---|---|---|
| 5,545,396 A | 8/1996 | Albert et al. |
| 5,612,103 A | 3/1997 | Driehuys et al. |
| 5,642,625 A | 7/1997 | Cates et al. |
| 5,809,801 A | 9/1998 | Cates et al. |
| 6,079,213 A | 6/2000 | Driehuys et al. |
| 6,085,743 A | 7/2000 | Chupp et al. |
| 6,295,834 B1 | 10/2001 | Driehuys |
| 6,423,387 B1 | 7/2002 | Zollinger |
| 6,467,479 B1 | 10/2002 | Albert et al. |
| 6,551,559 B1 | 4/2003 | Cates et al. |
| 6,581,599 B1 | 6/2003 | Stenzler |

FOREIGN PATENT DOCUMENTS

WO 2004/010045 1/2004

OTHER PUBLICATIONS

Hedlund, et.al., MR-compatible ventilator for small animals; computer controlled ventilation for proton and noble gas imaging, 18 Magnetic Resonance Imaging, pp. 753-759 (2000).

(Continued)

*Primary Examiner*—Justine R. Yu
*Assistant Examiner*—Kristen Matter
(74) *Attorney, Agent, or Firm*—Robert F. Chisholm

(57) ABSTRACT

Ventilator systems include: (a) a mass flow controller; (b) a gas delivery valve in communication with the mass flow controller and configured to selectively dispense a plurality of different gases to a subject; (c) a first gas source in fluid communication with the gas delivery valve; (d) a second gas source in fluid communication with the gas delivery valve; (e) a first pressure sensor located upstream of the gas delivery valve; (f) a second pressure sensor located downstream of the gas delivery valve; and (g) a controller operatively associated with the first and second pressure sensors and the mass flow controller, the controller comprising computer program code that monitors the pressures measured by the first and second pressure sensors and automatically dynamically adjusts the flow rate of the mass flow controller.

27 Claims, 26 Drawing Sheets

OTHER PUBLICATIONS

Hedlund, et.al., Three-dimensional MR microscopy of pulmonary dynamics, Society of Magnetic Resonance (New York, NY 1996).

Hedlund, et.al., Poster at the Amer. Thoracic society 1998 International Meeting (Chicago, 1998) MRI of pulmonary airways with hyperpolarized helium; a computer-controlled ventilator for imaging synchronous gas delivery in animal studies (describing ventilator technology).

Kwang, et.al., Gas Mixing for Biomedical Application Using Mass Flow Controllers medical and Biological Engineering and Computing, Peter Peregrinus Ltd., Stevenage, GB vo. 27, No. 6, Nov. 1, 1989 pp. 634-636.

Black, et.al., In vivo He-3 MR Images of Guinea Pig Lungs, Radiology, 199(3), pp. 867-870 (1996).

Int'l Search Report PCT/US2004/012237 dated Oct. 14, 2004.

BASIC COMPONENTS OF A BREATH

CYCLE WITH HOLD BREATH AND TRIGGERS

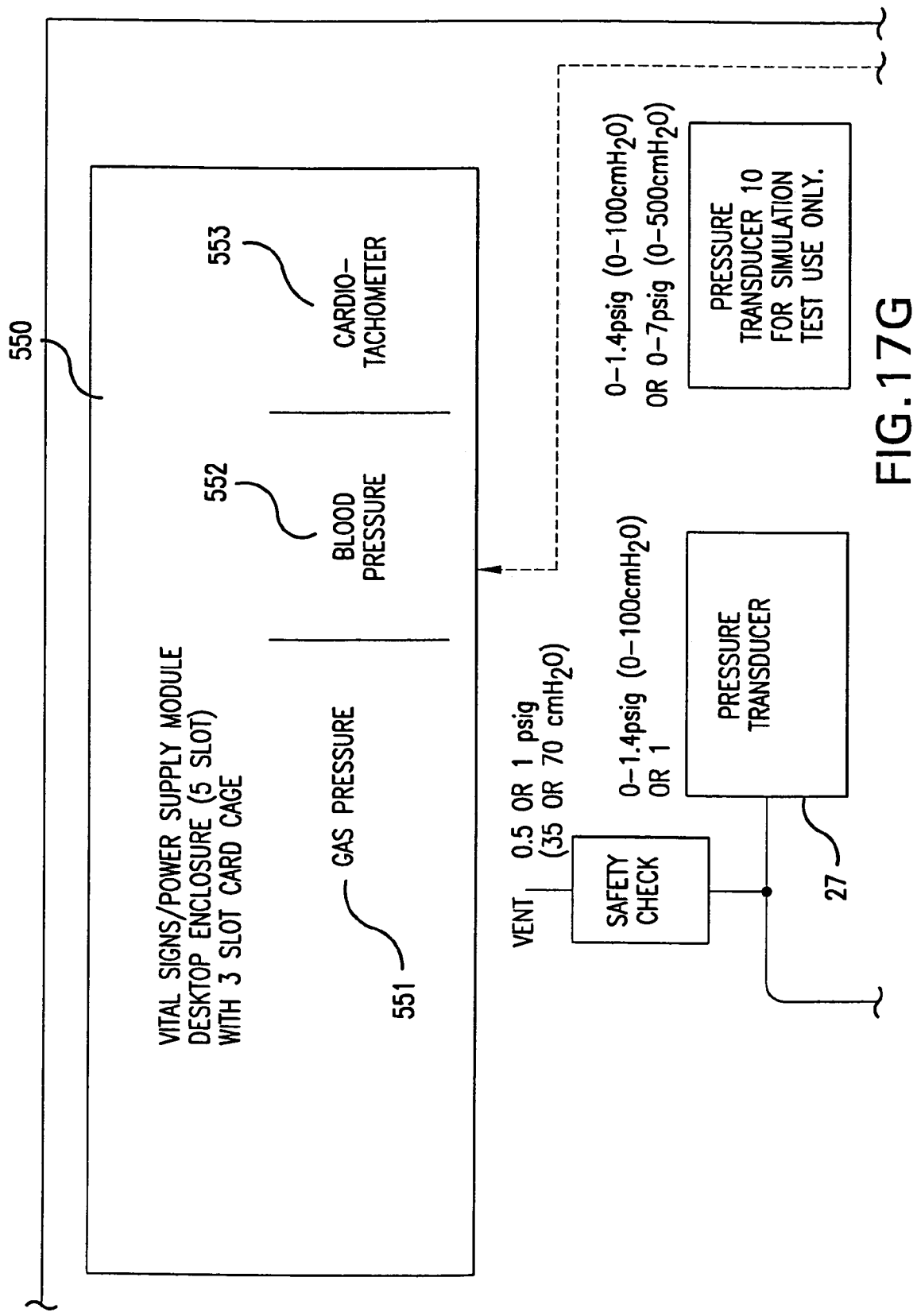

MRI/NMR-COMPATIBLE, TIDAL VOLUME CONTROL AND MEASUREMENT SYSTEMS, METHODS, AND DEVICES FOR RESPIRATORY AND HYPERPOLARIZED GAS DELIVERY

FIELD OF THE INVENTION

The present invention relates to the delivery of polarized noble gases to subjects for evaluations using NMR spectroscopy and/or magnetic resonance imaging ("MRI").

BACKGROUND OF THE INVENTION

Polarized inert noble gases can produce improved NMR signals in and/or MRI images of certain areas and regions of the body. Noble gases, such as polarized helium-3 ("$^3$He") and xenon-129 ("$^{129}$Xe"), have been found to be particularly suited for this purpose. Unfortunately, the polarized state of the gases is sensitive to handling and environmental conditions and can, undesirably, decay from the polarized state relatively quickly.

Hyperpolarizers are used to produce and accumulate polarized noble gases. Hyperpolarizers artificially enhance the polarization of certain noble gas nuclei (such as $^{129}$Xe or $^3$He) over the natural or equilibrium levels, i.e., the Boltzmann polarization. Such an increase is desirable because it enhances and increases the MRI signal intensity, allowing physicians to obtain better images of the substance in the body. See U.S. Pat. Nos. 5,545,396; 5,642,625; 5,809,801; 6,079,213, and 6,295,834; the disclosures of these patents are hereby incorporated by reference herein as if recited in full herein.

In order to produce the hyperpolarized gas, the noble gas can be blended with optically pumped alkali metal vapors such as rubidium ("Rb"). These optically pumped metal vapors collide with the nuclei of the noble gas and hyperpolarize the noble gas through a phenomenon known as "spin-exchange." The "optical pumping" of the alkali metal vapor is produced by irradiating the alkali-metal vapor with circularly polarized light at the wavelength of the first principal resonance for the alkali metal (e.g., 795 nm for Rb). Generally stated, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange." Alternative polarization enhancement techniques may also be used.

After the polarization process, the hyperpolarized gas is typically separated from the alkali metal (where spin-exchange techniques have been employed) prior to administration to a patient to form a non-toxic pharmaceutically acceptable product. Unfortunately, during production and/or during and after collection, the hyperpolarized gas can deteriorate or decay relatively quickly (lose its hyperpolarized state) and therefore must be handled, collected, transported, and stored carefully.

In the past, several researchers have used hyperpolarized gas compatible ventilators for delivering polarized gas to subjects to image hyperpolarized noble gases such as helium and xenon. For example, Hedlund et al., in *MR-compatible ventilator for small animals; computer controlled ventilation for proton and noble gas imaging,* 18 Magnetic Resonance Imaging, pp. 753-759 (2000), state that ventilators have been in routine use in their laboratory for a number of years. See also, Hedlund et al., *Three-dimensional MR microscopy of pulmonary dynamics,* Society of Magnetic Resonance (New York, N.Y., 1996); and a poster presented by Hedlund et al. at the Amer. Thoracic Society 1998 International Meeting (Chicago, 1998), entitled *MRI of pulmonary airways with hyperpolarized helium; a computer-controlled ventilator for imaging synchronous gas delivery in animal studies* (describing ventilator technology). In addition, Black and co-workers have used a hyperpolarized gas-compatible ventilator to generate what is believed to be the first ever in vivo images of hyperpolarized $^3$He in guinea pig lungs. See Black et al., *In vivo He-3 MR images of guinea pig lungs,* Radiology, 199(3), pp. 867-870 (1996). One known commercial small animal ventilator that may have been modified to dispense hyperpolarized gas and other respiratory gases have been is believed to be available from CWE Inc. (Ardmore, Pa.) as Model SAR-830.

Unfortunately, conventional small animal ventilators used to deliver hyperpolarized gases do not provide a way to accurately determine the volume delivered to the animal. Generally stated, conventional ventilators cannot adequately determine the volume delivered to the animal lungs separate from the volume delivered by the system itself. For example, certain conventional ventilators have proposed using flow meters with pressure transducers that control inspiration pressure and calculate an estimated volume by averaging the flow output to the subject over time. The variability in such an estimate may be undesirable, particularly when the amount of delivered polarized gas is small and the MRI/NMR signal depends on the amount, concentration and polarization level of polarized gas delivered, such as is the case for polarized gas investigations of small animals using millimole concentration ranges.

Thus, there remains a need for systems that can more accurately determine the amount of a gas and/or number of moles of gas delivered to an animal's lungs.

SUMMARY OF THE INVENTION

Embodiments of the present invention can provide improved MRI compatible hyperpolarized gas delivery systems, methods, and computer program products that can calculate ventilation-dispensed polarized gas volumes based on (automated) measurements taken in situ at the animal delivery site to provide one or more of: (a) a known or calculated inspiration or tidal volume of gas; (b) automated controlled volumetric delivery; (c) in situ real-time or dynamic adjustment of flow rate based on pressure and volume parameters; and (d) controlled ventilation to provide blends or selectable respiratory gases, including at least one hyperpolarized gas.

Certain embodiments of the present invention include a feedback pressure or flow rate control system that can automatically monitor inlet and outlet pressures to adjust the flows to maintain a steady state condition during measurement/calculation (i.e., flow in=flow out). Thus, embodiments of the present invention can maintain the system at a substantially constant pressure upstream of the gas delivery valve based on an automated in situ assessment of parameters associated with the system.

Particular embodiments of the present invention are configured with a tunable capacitance system to provide steady state pressure for controlled delivery of polarized gas or gas blends. The capacitance may be provided by a fluid-filled syringe that acts as a tuning capacitor with fluid that is added or subtracted from the system flow path.

The inspiration pressure can be set and a known volume delivered and/or the inspiration volume can be set and a known pressure delivered.

Certain embodiments of the present invention are directed to ventilator systems having a ventilation flow path for ventilating a subject. The systems include: (a) a mass flow controller; (b) a gas delivery valve in communication with the mass flow controller and configured to selectively dispense a plurality of different gases to a subject; (c) a first gas source in fluid communication with the gas delivery valve; (d) a second gas source in fluid communication with the gas delivery valve; (e) a first pressure sensor located upstream of the gas delivery valve; (f) a second pressure sensor located downstream of the gas delivery valve; and (g) a controller operatively associated with the first and second pressure sensors and the mass flow controller a controller operatively associated with the first and second pressure sensors and the mass flow controller, the controller configured to monitor the pressures measured by the first and second pressure sensors and the flow rate of the mass flow controller and automatically determine a delivered tidal volume using a reading of the flow rate of the mass flow controller when the first pressure is at a substantially steady state condition.

The system can also include a tracheal tube and the controller can be configured to adjust the flow rate to generate a substantially constant pressure at the first pressure sensor during delivery of the polarized gas.

Other embodiments are directed to methods of delivering hyperpolarized gas to a subject. The methods include: (a) providing a ventilator system with a mass flow controller, a tracheal tube and a gas delivery valve configured to deliver hyperpolarized gas and at least one non-polarized gas to a subject; (b) monitoring a first pressure in the ventilator system upstream of the gas delivery valve; (c) monitoring a second pressure in the ventilator system downstream of the gas delivery valve; (d) obtaining a reading of the mass flow controller when the first pressure is substantially constant; and (e) automatically determining the tidal inspiration volume of hyperpolarized gas delivered to the subject in situ using the obtained mass flow controller reading.

Other embodiments are directed to a system for delivering hyperpolarized gas to a subject, including: (a) a gas delivery valve configured to deliver hyperpolarized gas and at least one non-polarized gas to a subject; (b) a mass flow controller disposed upstream of the gas delivery valve; (c) a tracheal tube disposed downstream of the gas delivery valve; (d) means for monitoring a first pressure in the ventilator system upstream of the gas delivery valve; (e) means for monitoring a second pressure in the ventilator system downstream of the gas delivery valve; (f) means for automatically obtaining readings of the mass flow controller; and (g) means for automatically determining the tidal inspiration volume of hyperpolarized gas delivered to the subject in situ using the monitored first pressure and the value of a reading of the mass flow controller obtained when the first pressure is substantially constant.

In certain embodiments, the ventilator system can include a variable mass flow controller disposed upstream of the gas handling valve and the method can be carried out to automatically dynamically adjust the flow rate of the mass flow controller to maintain a substantially constant first pressure during ventilation delivery of the hyperpolarized gas to the subject.

The system and/or method can also operate to accept user input to select a desired operational mode such as either a tidal volume operational mode with the desired tidal volume selected or a peak inspiration pressure operational mode with the desired peak inspiration pressure selected.

Still other embodiments are directed to ventilator systems having a ventilation flow path for ventilating a subject. The systems include: (a) a gas delivery valve configured to selectively dispense a plurality of different gases to a subject; (b) a mass flow controller disposed upstream of the gas delivery valve; (c) a first polarized source in fluid communication with the gas delivery valve; (d) a second gas source in fluid communication with the gas delivery valve; (e) a first pressure sensor located upstream of the gas delivery valve; (f) a second pressure sensor located downstream of the gas delivery valve; and (g) a manifold line having a fluidic tunable capacitance disposed upstream of the gas delivery valve. The fluidic capacitance has a volume that is at least about 10 times greater than the volume of the lungs of the subject.

The system can include at least one fixed volume reservoir (or line) that is configured to selectively engage the manifold to adjust the fluidic capacitance responsive to pressure measurements obtained by the first and second pressure sensors. The system may include a syringe with a quantity of fluid therein with the syringe being in communication with the manifold line and configured to selectively add or remove fluid from the manifold.

All, or selected operations, features, functions and/or configurations of the embodiments described above may be carried out as methods, systems, computer program products, assemblies and/or devices as contemplated by the present invention.

The foregoing and other objects and aspects of the present invention are explained in detail herein.

BRIEF DESCRIPTION OF THE DRAWINGS

FIGS. 17A-I are to be arranged so as to depict a schematic illustration of an automated ventilator system according to embodiments of the present invention.

FIGS. 17A-I depict portions of the schematic illustration to be assembled according to FIG. 17.

DETAILED DESCRIPTION OF EMBODIMENTS OF THE INVENTION

Figure 1:
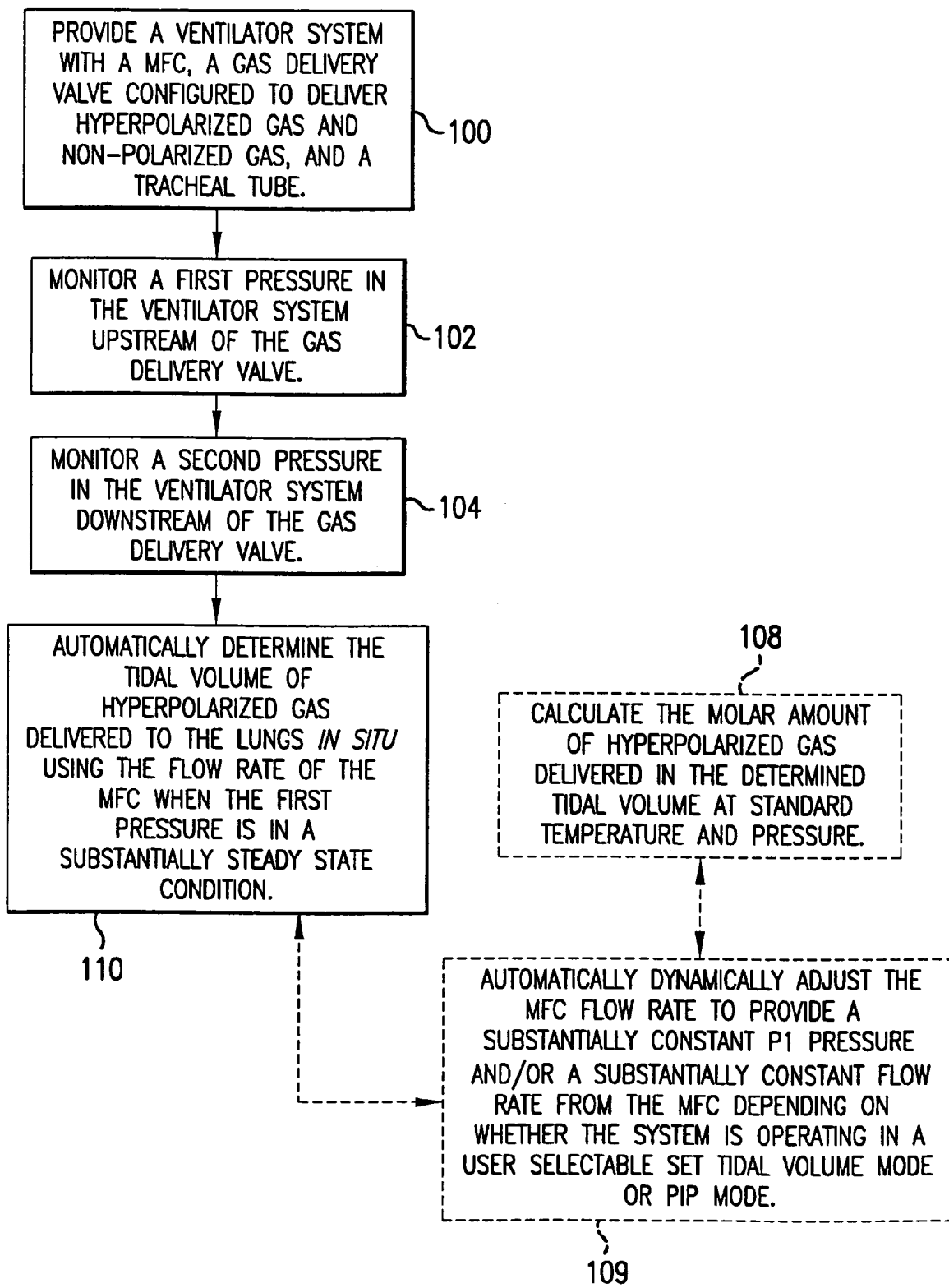
FIG. 1 is a block diagram of operations that can be carried out according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the drawings, layers, regions, or components may be exaggerated for clarity. In the figures, broken lines indicate optional features unless described otherwise.

In the description of the present invention that follows, certain terms may be employed to refer to the positional relationship of certain structures relative to other structures. As used herein the term "forward" and derivatives thereof refer to the general direction the target gas or target gas mixture travels as it moves through the ventilator system; this term is meant to be synonymous with the term "downstream," which is often used in manufacturing environments to indicate that certain material being acted upon is farther along in the manufacturing process than other material. Conversely, the terms "rearward" and "upstream" and derivatives thereof refer to the directions opposite, respectively, the forward and downstream directions.

Also, as described herein, polarized gases are produced and collected and may, in particular embodiments, be frozen, thawed, used alone and/or combined with other constituents, for MRI and/or NMR spectroscopy applications. As also used herein, the term "polarized gas" includes at least one polarized gas of interest (such as, but not limited to, $^3$He and/or $^{129}$Xe) and may include one or more other constituents such as other carrier, blending or buffer gases. Further, the terms "polarize", "polarizer", "polarized", and the like are used interchangeably with the terms "hyperpolarize", "hyperpolarizer", "hyperpolarized" and the like.

The ventilator systems and gas delivery valves contemplated by the present invention can be used for any target subjects and are hyperpolarized gas-compatible for NMR and/or MRI procedures. Although described herein for ease of discussion as a single gas delivery valve for delivering selectable ventilation gases, a plurality of discrete valves may also be used. "Subjects", according to the present invention, can be any animal subject, and are preferably mammalian subjects (e.g., humans, canines, felines, bovines, caprines, ovines, equines, rodents, porcines, and/or lagomorphs). The term "small animals" includes mice, rats, guinea pigs, dogs, cats, monkeys, pigs, and rabbits.

Various techniques have been employed to accumulate and capture polarized gases. For example, U.S. Pat. No. 5,642,625 to Cates et al. describes a high volume hyperpolarizer for spin-exchange polarized noble gas and U.S. Pat. No. 5,809,801 to Cates et al. describes a cryogenic accumulator for spin-polarized $^{129}$Xe. As used herein, the terms "hyperpolarize," "polarize," and the like, are used interchangeably and mean to artificially enhance the polarization of certain noble gas nuclei over the natural or equilibrium levels. Such an increase is desirable because it allows stronger imaging signals corresponding to better NMR spectroscopy and/or MRI images of the substance and a targeted area of the body. As is known by those of skill in the art, hyperpolarization can be induced by spin-exchange with an optically pumped alkali-metal vapor or alternatively by metastability exchange. See Albert et al., U.S. Pat. No. 5,545,396.

In particular embodiments, the ventilated polarized gas may be a noble gas, such as $^{129}$Xe or $^3$He. Other gases and/or noble gases may also be used, alone or in combination. Buffer gas formulations may also be used as described in U.S. Pat. No. 6,295,834, the contents of which are hereby incorporated by reference as if recited in full herein. In other embodiments, the polarized gas may comprise $^{13}$C and/or $^{15}$N compounds, such as organic molecules enriched in $^{13}$C, which may be polarized using dynamic nuclear polarization (DNP) and/or para-hydrogen induced polarization.

FIG. 1 illustrates operations that can be performed according to embodiments of the present invention. As shown, a ventilator system with a MFC ("mass flow controller"), tracheal tube and a gas delivery valve configured to (selectively) deliver hyperpolarized gas and a non-polarized gas is provided (block 100). A first pressure in the ventilator system upstream of the gas delivery valve is monitored (block 102). A second pressure in the ventilator system downstream of the gas delivery valve is monitored (block 104). The tidal volume of hyperpolarized gas delivered to the lungs can be automatically determined in situ using the flow rate of the MFC when the first pressure is in a substantially steady state condition (block 110). Steady state means that the pressure variation is within a desired tolerance such that it neither increases nor decreases over time during a desired interval. In certain embodiments, the ventilator system automatically controls and adjusts the MFC flow rate dynamically so as to maintain a substantially constant first pressure during delivery of the hyperpolarized gas. The system may automatically dynamically adjust the MFC flow rate to selectively provide a substantially constant P1 pressure and/or a substantially constant flow rate from the MFC depending on whether the system is operating in a user-selectable set tidal volume mode or a PIP mode (block 109).

The molar amount of hyperpolarized gas delivered in one or more tidal volumes (the tidal volume can be described as the change in volume during each breath) can be calculated based on the determined tidal volume using the MFC data and adjusted to be at standard temperature and pressure (block 108). That is, the tidal volume can be measured at standard temperature and pressure and this value can be translated into moles at this volume at standard temperature and pressure to evaluate the number of moles of hyperpolarized gas delivered the subject's lungs is determined. The measured amount can be in the millimole range for small animal ventilation.

Figure 2A:
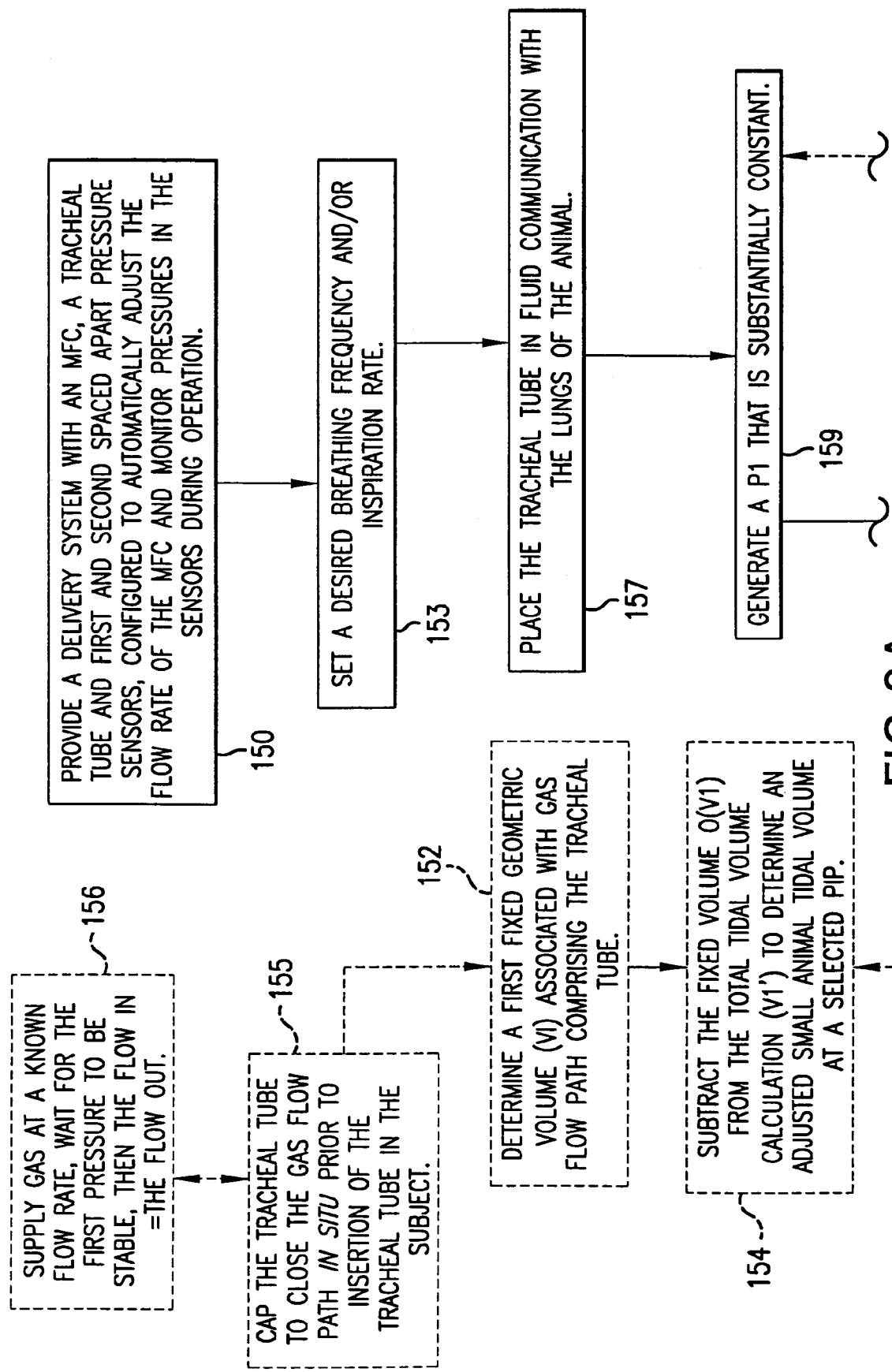
FIGS. 2A-B are a block diagram of operations that can be carried out according to additional embodiments of the present invention.
Figure 2B:
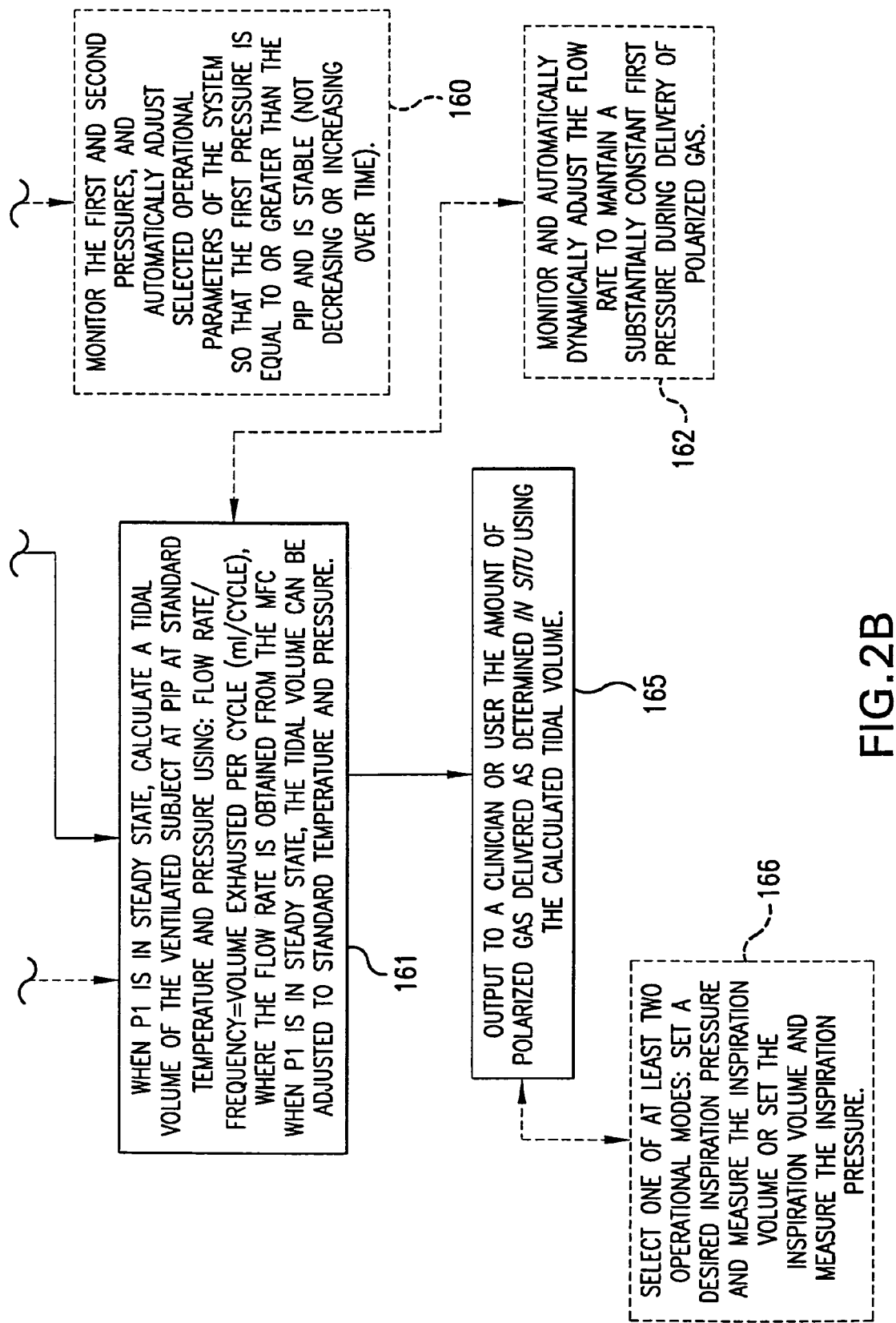

FIGS. 2A-B illustrate operations that can be carried out to operate a ventilator and deliver hyperpolarized gas according to other embodiments of the present invention. Similar to the embodiment discussed above, the ventilator delivery system can include an MFC, a tracheal tube and first and second spaced apart pressure sensors (one located upstream of the gas delivery valve and/or tracheal tube and one located downstream of the gas delivery valve and/or on or in the tracheal tube). The sensors can be configured to automatically measure respective first and second pressures, P1, P2, in the ventilator system during operation. A desired breathing cycle, rate and/or inspiration rate can be set (i.e., breath per minute "BPM" and inspiration/expiration "I/E" ratio) (block 153). The tracheal tube can be positioned in the subject (before, during or after the operational mode is selected), in fluid communication with the lungs thereof (block 157). The MFC flow rate can be adjusted to provide a substantially constant P1 (block 159). When P1 is in steady state, the tidal volume of the ventilated subject can be calculated or determined at PIP (peak inspiration pressure) at standard temperature and pressure using flow rate/frequency=volume exhausted/cycle (typically in units of ml/cycle—although other units can be used) (block 161). The delivered amount of hyperpolarized gas can be output in situ using the calculated tidal volume (block 165).

A predetermined portion of the ventilation system gas flow path including the tracheal tube defines a first static geometric volume "V1" (block 152). In operation, the first geometric volume "V1" can be subtracted from the calculated tidal volume V1' (block 154), which is the volume of gas exhausted during a (each) breath for a particular one or more PIP. The volumetric correction can provide a more representative or "truer" tidal volume delivered to small animals where small amounts can influence the results. The fixed geometry volume V1 can be calculated using known or measured dimensions or dynamically determined when the first pressure stabilizes with the tracheal tube closed.

In particular embodiments, a distal portion of the tracheal tube (the end that will be the deepest in the subject) can be capped or otherwise closed in situ, prior to insertion into the subject (block 155). That is, V1' can be determined using the value of the MFC when P1 is in steady state operation. Because the downstream geometric volume is constant (with the tube closed), V1 can be calculated from the change in pressure between PIP and atmospheric pressure. A selected gas can be delivered during the V1 fixed geometry evaluation at a known flow rate, when the first pressure and the peak inspiration pressure (measured at P2) stabilize or are in steady state during PIP, then flow in will equal the flow out (i.e., the flow during inspiration equals the flow during expiration) (block 156).

The first and second pressures can be monitored and the data used to automatically and dynamically adjust selected operational parameters of the system so that the desired peak inspiration pressure is reached and the first pressure is stable (block 160). The dynamic adjustment(s) can be carried out to maintain a substantially constant first pressure during delivery of the polarized gas (block 162). The system can be operated on different selectable modes that can be set by the user; thus, the system can be operated via a set inspiration pressure mode, where the inspiration volume is determined, or measured, or a set tidal (inspiration) volume mode, where the inspiration pressure is measured (block 166).

In any event, when the tidal volume is measured, the "total" tidal volume V1' is measured (primarily representing the volume downstream of the gas delivery valve). The volumetric contribution of the tube V1 may be subtracted at a particular PIP. For medium or large animals the volumetric correction for the tube may not be required.

Figure 3A:
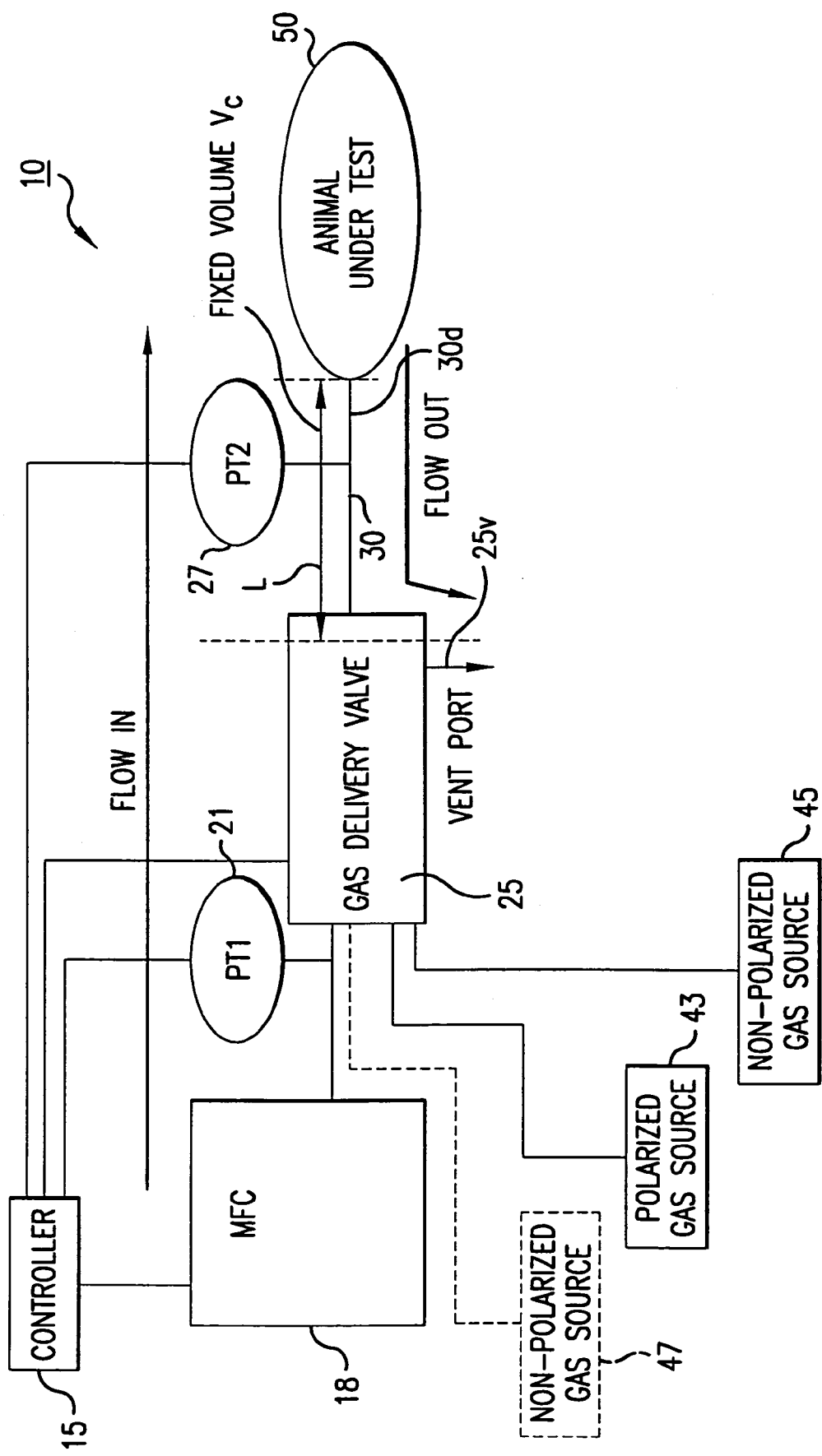
FIG. 3A is a schematic illustration of a ventilator delivery system according to embodiments of the present invention.

FIG. 3A illustrates one embodiment of a ventilator system 10. As shown, the system 10 includes a controller 15, a variable mass flow controller (MFC) 18, a first pressure sensor 21 (shown as a pressure transducer PT1), a gas delivery valve 25, a second pressure sensor 27, and a tracheal tube 30. The gas delivery valve 25 is in fluid communication with a polarized gas source 43 and a non-polarized gas source 43. In certain embodiments, the gas delivery valve 25 may optionally be in communication with additional gas sources (designated herein at feature 47). The mass flow controller 18 can be a variable calibrated mass flow controller, such as a voltage controlled controller p/n DFC2600 available from AALBORG located in Orangeburg, N.Y.

FIG. 3A also illustrates the direction of flow in and flow out of the subject (shown by the arrows), shown as an animal subject 50. During exhale or expiration the exhaust is directed out of the subject back through the tracheal tube 30 and out of the gas delivery valve 25 via vent port 25v. The vent port 25v may be in fluid communication with a gas sensor (not shown) that determines exhaled gas contents, concentration or ratios.

Generally described, in operation, a control feedback system is used to adjust the rate of flow of the mass flow controller 18 to control delivery of a desired volume to the subject. The feedback is based on monitored pressure readings of the first and second pressure sensors 21, 27. The first sensor 21 is disposed upstream of the gas delivery valve 25 proximate the mass flow controller 18. The second sensor 27 is located downstream of the gas delivery valve 25 proximate the animal 50. The sensor 27 can be a pressure transducer or other type of pressure sensor. In certain embodiments, the second pressure sensor 27 can be positioned in or on the endotracheal tube itself so as to be able to measure the pressure in the lungs by placing the sensor 27 as close to the source or target as possible. However, in certain particular embodiments, such as when the tracheal tube diameter is very small such as for use with mice and the like, the sensor 27 may be positioned upstream of the lungs. A port can be added to the gas delivery valve that connects to the tracheal tube through the valve body.

The operational premise of "flow in=flow out" can be used in certain situations. Flow in means flow into the volume of the gas flow path upstream of the gas delivery valve from the MFC and flow out means flow out of the volume downstream of the gas delivery valve. If the pressure at the first sensor 21 continues to increase during ventilation, then the flow rate is too great and the controller 15 can dynamically reduce the flow. If the pressure at the first sensor 21 decreases during ventilation, then additional flow is needed and the controller 15 can dynamically increase the flow. If the pressure at the first and/or second sensors 21, 27 reaches a steady state condition during a peak inspiration pressure calculation, then the proper flow is being used.

Readings of the mass flow controller 18 are based on a calibrated gas at standard pressure (1 ATM, 14.7 psia, 1033.51 cm $H_2O$) and temperature (70 degrees F.). The temperature and pressure can be monitored and adjustments made (the readings normalized to the standard pressure and temperature) as suitable. For an initial or "first pass" operational set-up or evaluation, temperature effects can be assumed to be nominal. If the calibrated gas is not the gas used for output, a conversion constant can be applied to determine the flow set point. For example, if the mass flow controller 18 is calibrated for nitrogen but helium is used, then a conversion factor of 1.454 is used in the calculations. Table 1 lists examples of a conversion "K" factor for default settings (standard temperature and pressure) that can be used in calculating parameters used to operate the ventilator.

TABLE 1

K Factors

| GAS | K Factor based on $N_2$ calibration gas |
|---|---|
| Air | 1.0000 |
| AR | 1.4573 |
| He | 1.4540 |
| $N_2$ | 1.0000 |
| $N_2O$ | 0.7128 |
| $O_2$ | 1.0000 |

Figure 3B:
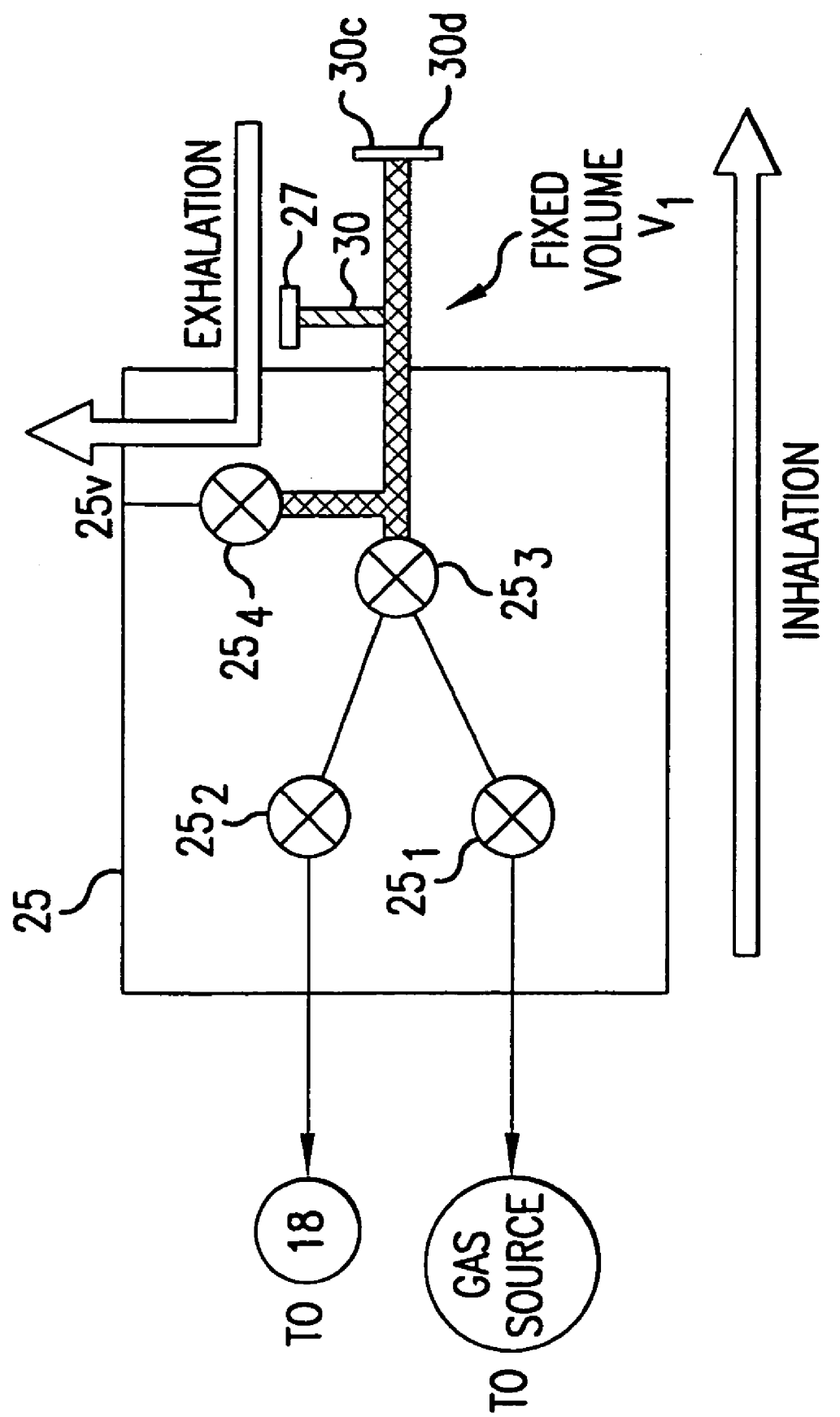
FIG. 3B is a schematic illustration of a portion of a ventilator system with a tracheal tube and gas delivery valve that can be used to define a fixed volume according to embodiments of the present invention.

FIG. 3B illustrates that a calibration pressure P1 can be established when the tracheal tube 30 is capped (shown with an end cap 30c) and disposed outside of the body of the subject with the tracheal tube 30 closed (via cap, valve or other means) to close the exit end of the tracheal tube 30 while attached to the system 10 defining a first fixed system volume "V1" that can also be described as a calibration volume Vc (and sometimes described as Vcal hereinafter). The calibration volume Vc is associated with a predetermined portion of the ventilator system gas flow path having a fixed geometry as shown in FIG. 3A. Typically, the calibration volume Vc is that portion of the gas flow path has a length "L" that extends through a portion of the gas delivery valve 25 to the distal end 30d of the tracheal tube 30. The length may be about 12 inches. The endotracheal tube 30 may be formed of 1/16 inch inner diameter tubing that can releaseably connect to the valve 25 via a male luer lock (not shown). FIG. 3B illustrates one embodiment of a gas delivery valve 25 with a plurality of individually selectable gas valves $25_1$, $25_2$, $25_3$. The fixed volume V1 in this embodiment is the volume indicated by the cross-hatched portion of the flow path, which includes the flow path extending downstream of or in advance of the valve $25_3$ to the distal end 30d of the tracheal tube 30 in the forward input flow direction and includes the connection to the pressure transducer 27 and, in the exhaust or output direction, from the tracheal tube to the valve $25_4$ associated with vent port 25v.

Figure 4:
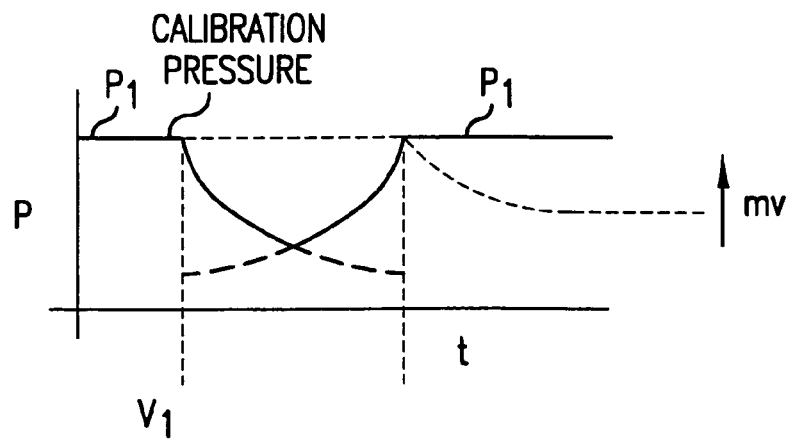
FIG. 4 is a graph of pressure versus time illustrating volumetric changes to a ventilation system according to embodiments of the present invention.

After the tracheal tube 30 is placed in operative position, in fluid communication with the lungs of the subject, the lungs have an associated tidal volume that changes during a breath, this volume is added to the first system volume V1 to provide a total tidal volume V1'. FIG. 4 graphically illustrates the addition of this volume to the ventilator system 10. That is, absent the pressure feedback control system, the system 10 with the tracheal tube 30 open and in the lungs delivers to a larger reservoir volume at the same flow rate thereby causing the pressure to decrease (shown by the fall in pressure noted in FIG. 4 when V2 is added). However, the flow rate can be increased to again bring (or keep) the system 10 at a desired substantially constant pressure, as shown in FIG. 4 as the pressure returns to the P1 value and levels off with the lungs added to the system (when the tracheal tube is open and in position in the subject).

Figure 5A:
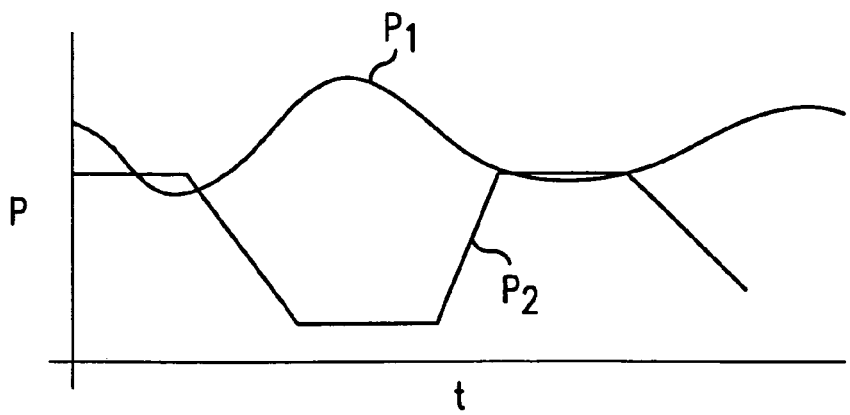
FIG. 5A is a graph of pressure versus time illustrating variable systemic pressures in response to inspiration and/or expiration pressures.
Figure 5B:
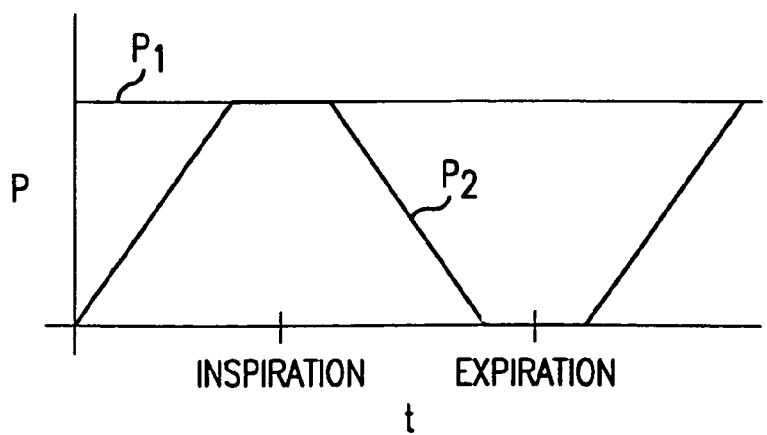
FIG. 5B is a graph of pressure versus time illustrating systemic and PIP pressures during ventilation according to embodiments of the present invention.

FIGS. 5A and 5B illustrate the pressure P1 at the first sensor 21 in relation to the pressure at the second sensor 27 over time (t) during operation with the tracheal tube 30 in position in the subject. The pressure P2 at the second sensor 27 is made in the subject's airway during operation and corresponds to the BPM and I/E ratio selected. The maximum P2 pressure is the peak inspiration pressure (PIP). FIG. 5A illustrates pressure fluctuation in the first pressure that may cause measurement errors. FIG. 5B illustrates the system 10 being controlled to provide a substantially constant operating or system pressure P1, with P1 being steady state or stable (not increasing or decreasing over time) and substantially equal to and/or greater than the PIP according to embodiments of the present invention. In certain embodiments, this P1 pressure stability can be carried out using a capacitance volume located upstream of the gas delivery valve as will be discussed further below. The size of the capacitance can be tuned to reduce the fluctuations of P1 shown in FIG. 5A so that P1 behaves more like that shown in FIG. 5B. It is noted that oversizing the capacitance may slow the responsiveness of the system.

Referring back to FIG. 3A, in certain embodiments, the first sensor 21 can be a pressure transducer PT1 that is used to monitor the pressure in the system 10 between the mass flow controller 18 and the gas delivery valve 25 based on the flow into the gas delivery valve 25. The second sensor 27 can also be a pressure transducer, PT2, and can be used to monitor the airway pressure from the subject (which can be an animal). The gas delivery valve 25 can be configured for either supplying the air to the subject and/or for allowing the subject to hold breath or exhale.

Figure 6:
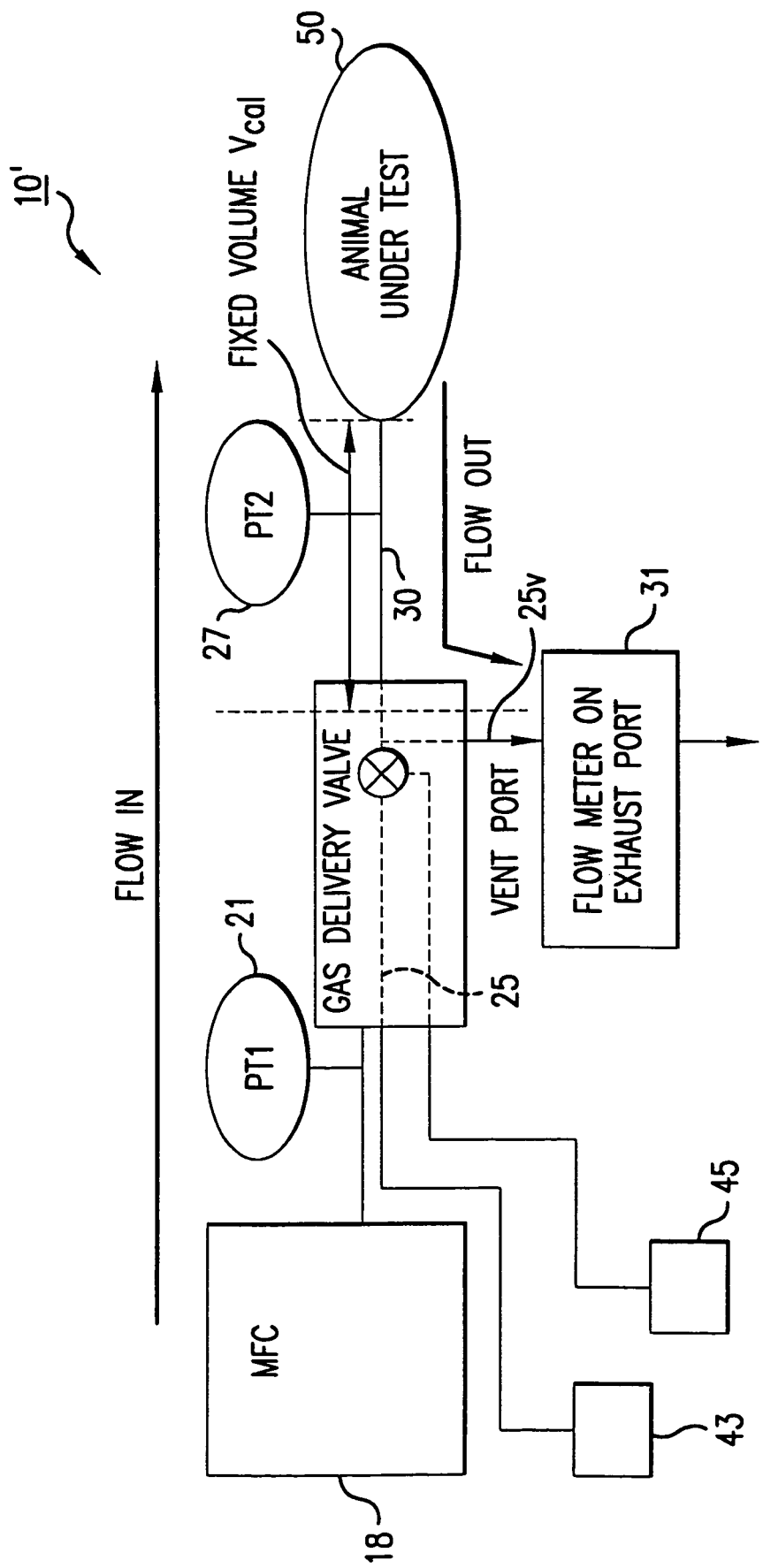
FIG. 6 is a schematic illustration of a controller/interface module according to embodiments of the present invention.

FIG. 6 illustrates an alternative embodiment of a ventilator system 10' using a flow meter 31 in-line with either a source of supply gas(es) (not shown) and/or a vent port 25v. Other embodiments can use an independent flow meter and a proportional valve (not shown). Still other embodiments can employ manually adjustable flow valves (also not shown). Combinations of the above may also be used.

The lung volume can vary with PIP and BPM as lungs are typically somewhat elastic. Thus, an a priori evaluation of the animal expected lung physiological characteristics can be programmed to help establish flow rate adjustment increments and default operating parameters. For example, the ventilator system 10, 10' can be operatively associated with a reference library of animal characteristics, such as, but not limited to, estimated lung volume versus pressure, PIP, BPM, flow rates, and the like to help operate the feedback control system. An example of default parameters is listed in Table 2 below.

TABLE 2

Default Parameters

| Animal | Tidal Volume | BPM | I/E |
|---|---|---|---|
| Mice | 0.3 mL | 110 | 30/70 |
| Rats | 1.5 mL | 60 | 30/70 |
| Guinea Pigs | 4.0 mL | 50 | 30/70 |
| Rabbits | 18.0 mL | 35 | 30/70 |

Certain embodiments of the gas delivery valve 25 employ at least one spool or piston to actuate at least one gas flow path in a NMR/MRI compatible valve body. This configuration may be particularly suitable for small animal ventilators used during NMR spectroscopy and/or MRI imaging sessions. For additional description of a spool or shuttle valve, see U.S. Provisional Patent Application Serial No. 60/450,209 filed Feb. 26, 2003, the contents of which are hereby incorporated by reference as if recited in full herein. Other valve configurations, such as but not limited to, diaphragm and/or pincher valves may also be used.

In any event, the gas delivery valve 25 can be configured to provide fast response times, which may be particularly suitable for use in situations where the subject is ventilated at a high BPM breathing rate with a low inhale/exhale or inspiration/expiration ratio (I/E). The I/E ratio is the inspiration time over the expiration time. "Inspiration" is the time during which the gas is provided to the animal (or other subject) while "expiration" is the time during which the animal (or other subject) is exhaling. Therefore, a high BPM, such as about 180 BPM, means that each breath lasts 333 ms. An I/E of 20/80 means that the device has 67 ms to deliver the desired tidal volume to the animal (or other subject). The speed at which the valve opens can be important, as the faster the BPM, the smaller the I/E %, and the less time the valve has to open and supply the desired amount of gas to the animal (or other subject).

The I/E ratio is typically within about 30/70 to 60/40, but can vary outside of this range, depending on the desired result. The I/E ratio and BPM can be substantially fixed during "normal" (non-imaging) breathing. The BPM and I/E ratio can be adjusted to be different for imaging (hyperpolarized gas) breath runs, but once the image run is over, these operating parameters can return to "normal" breathing parameters. See FIGS. 11-14 for examples of breath cycles according to embodiments of the present invention.

Also, it is noted that 180 BPM may be an upper range for many small animal species and, in certain embodiments, the ventilators 10, 10' may operate at a lower rate. The operating parameters are animal species/weight driven. For example, mice use a faster BPM than a rabbit. The I/E ratio can change between animals but will typically stay within the range mentioned above. During NMR/MRI signal acquisition, the BPM may be about 30 BPM for a small animal such as a mouse.

In addition, the valve may be configured for an "on-off" operation of a single gas or different gases to deliver or hold back a single gas (typically hyperpolarized gas) or different gases and/or to open and close the single or plurality of gas flow paths (not shown) for controlled inhalation delivery to a subject; the gas delivery valve 25 can also be configured to select between inhale, exhale, and/or breath-hold ventilation operations.

The valve body and polarized gas flow path (including the tracheal tube 30) and its internal components can be formed from and/or coated with a material or materials selected for the ability to inhibit depolarization of hyperpolarized gas (such as due to relaxation attributed to gas interaction therewith). Coatings such as sol-gel coatings, deuterated polymer coatings, metal film coatings and other coatings and non-magnetic materials that inhibit depolarization can also be used. See, e.g., U.S. patent application Ser. No. 09/485,476 and U.S. Pat. Nos. 5,612,103 and 6,423,387, the contents of which are hereby incorporated by reference as if recited in full herein. For example, the valve body and/or components may be formed of materials such as, but not limited to, aluminum, TEDLAR, TEFLON, PTFE, DELRIN (acetal), and the like. Care should be taken to reduce the sources of friction by providing a smooth surface finish, and reducing the number of O-rings or selecting the O-ring material to reduce friction. In addition, the valve body can be fabricated to tolerances to provide sufficient seals and yet provide reduced friction between the spool and valve body receptacle. Thus, the valve body bore finishes, the interface with the endotracheal tube, any O-ring compression, and lubricants may all be considered to reduce the sources of friction. The endotracheal tube can also be configured from medical grade biocompatible materials, which are also configured with material(s) or coatings that inhibit hyperpolarized gas decay.

The valve 25 can be configured to automatically provide a selection of ventilation breath outputs and/or inputs according to embodiments of the present invention as directed by the controller 15. For discussion purposes, Gas A will be described as a hyperpolarized gas and Gas B as a non-polarized gas. In operation, a reverse configuration can be used. The term "breath-hold" means that the gas or gases are held in the lungs for a breath-hold time to facilitate bio-uptake of the gas and/or allow a stronger hyperpolarized gas signal relative to normal respiration. The breath-hold duration may be between 5-30 seconds.

The valve 25 can be actuated to accommodate: (a) Gas "A" inhale; (b) Gas "B" inhale; (c) Gas "A"+Gas "B" inhale; (d) exhale; (e) partial exhale and breath hold; (f) Gas "A" inhale and breath hold; (g) Gas "B" inhale and hold; and (h) Gas "A"+Gas "B" inhale and breath hold. As noted above, the hyperpolarized gas may be a hyperpolarized noble gas such as $^3$He and/or $^{129}$Xe. The non-polarized gas may be a mixture of non-polarized gases. The non-polarized gas can be selected to inhibit depolarization of the hyperpolarized gas, and may be also selected for biocompatibility. Examples of suitable non-polarized gases include, but are not limited to, nitrogen, xenon, and helium. The valve 25 may also be used to connect to an anesthetic vaporizer.

In addition, the valve 25 and polarized gas flow path in the ventilator system can be configured to reduce any dead volume for the inhaled gas(es). The term "dead volume" means the volume from source to subject such as within the valve or downstream system that needs to be filled with gas before the gas will reach the subject. The smaller the volume, the less gas that is "wasted". Reducing the dead volume is particularly desirable when dispensing hyperpolarized gas because the hyperpolarized gas fills the volume of the flow path from source to subject and any polarized gas remaining in the dead volume may become unpolarized or decay to an undesirable polarization level, and must be displaced before suitably polarized gas can reach the subject on the next polarized breath.

In certain embodiments, the ventilator system 10, 10' is configured to operate in an NMR/I suite having magnetic field strength up to about 5 T. In other embodiments, the ventilator 10, 10' can be configured to operate in a low magnetic field environment, typically under about 100 Gauss. The ventilator system 10, 10' can be configured to operate in intermediate field strengths as well, such as, but not limited to, greater than about 100 Gauss and up to about 1.5 T.

In certain embodiments, the ventilator system 10, 10' can be configured to provide a tidal volume control of from about 0.2 mL to about 100 mL, in 0.1 mL increments. The system 10, 10' may be configured to operate with a BPM range of from about 5-180, with about a 1 BPM adjustable increment. The system 10, 10' may also be configured to allow selectable inspiration/expiration ratios from between about 5:1 to 1:5 with about a 1% increment adjustability and supply controlled PIP of from about 0-40 inches H$_2$O with about 1 inch H$_2$O increments. The tidal volume flow can range from about 0-5 liters/min. The ventilator 10, 10' can be shielded so that EMI/RFI produced shall not unduly affect the polarization level of the gas or the operation of the MRI/NMR equipment.

Figure 7:
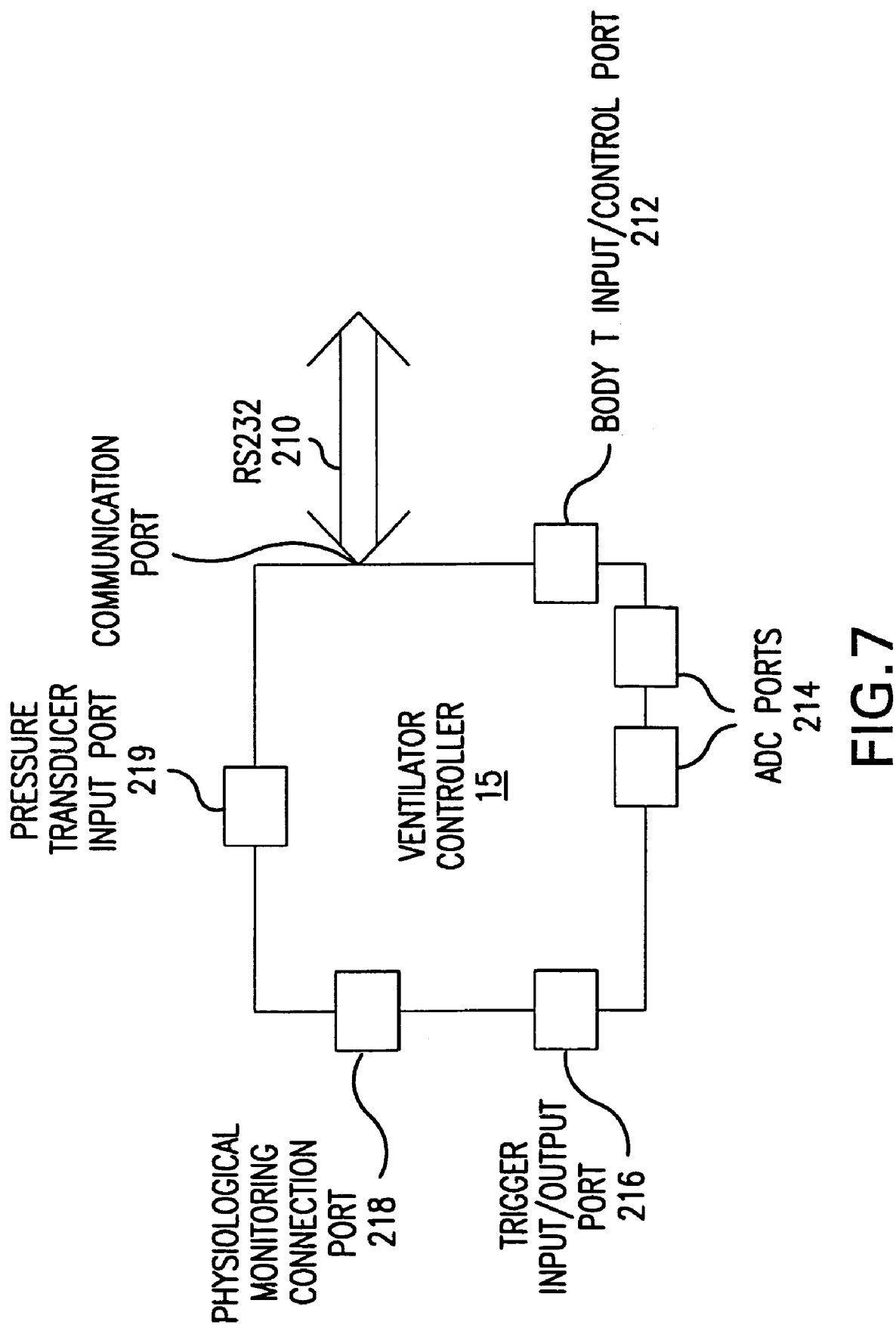
FIG. 7 is a schematic illustration of an alternate ventilator delivery system according to embodiments of the present invention.

FIG. 7 illustrates one configuration of a controller 15 according to certain embodiments of the present invention. As shown, the controller 15 can include at least one RS232 communication port 210, a body temperature monitoring port 212, a plurality of analog to digital and/or digital to analog ports 214, and a trigger input/output port 216 that can sequence or generate gated trigger signals to an NMR/MRI system during or prior to signal acquisition. The gated trigger signal can relate to a desired portion of a breath-hold cycle and/or an "R" trigger in a detected QRS cardiac rhythm. The controller 15 can also include a physiological monitor connection port 218 that accepts data regarding at least one of heart rate, ECG, blood pressure, oxygen saturation levels, CO$_2$ during expiration, body temperature, and the like, as well as a pressure transducer input port(s) 219.

The temperature monitor can monitor internal animal body temperature and direct heating and/or cooling of the animal to maintain the temperature within a desired range. The temperature monitor may be independent of the controller 15.

Figure 8:
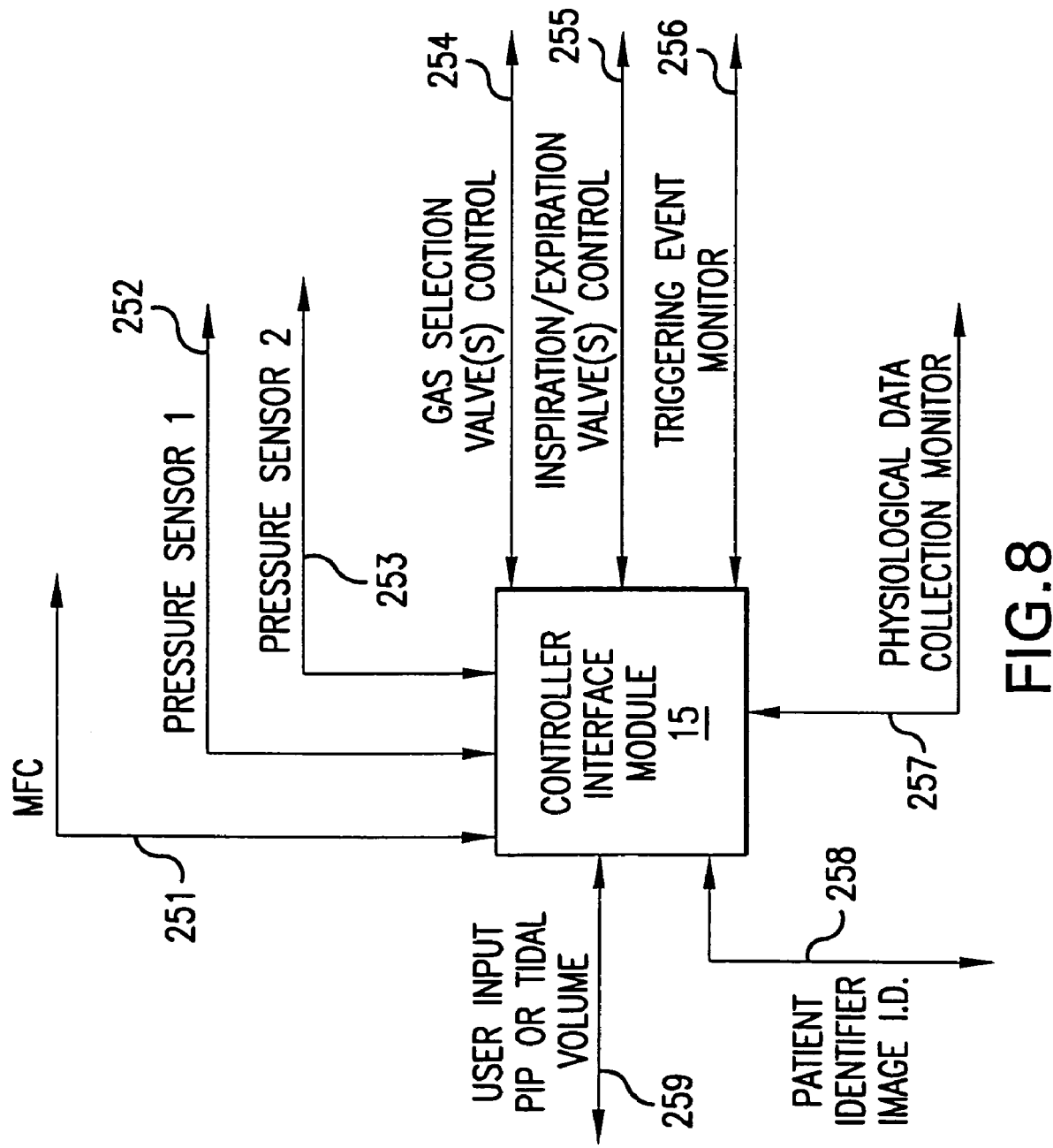
FIG. 8 is a block diagram of a controller port configuration for a ventilator according to embodiments of the present invention.

FIG. 8 illustrates one embodiment of a controller 15 with an interface module having a plurality of different interface connections to remote, peripheral and/or integrated devices. As shown, the connections or ports include a control line to the mass flow controller 251, a communication line between the first and second sensors 252, 253 and a control line to the gas delivery valve 254. The controller 15 can also have a gas delivery valve control line 255 configured to control and direct the flow direction, i.e., inspiration/expiration, a triggering event monitoring line 256, and a physiological data collection communication line 257. As shown, the controller 15 can also include a communication port to accept user input for operational parameters 259 and can include a communication port or line 258 that engages an NMR/MRI device or system lines to record tidal volume/PIP or other information on NMR/MRI signal acquisitions or images.

Figure 9:
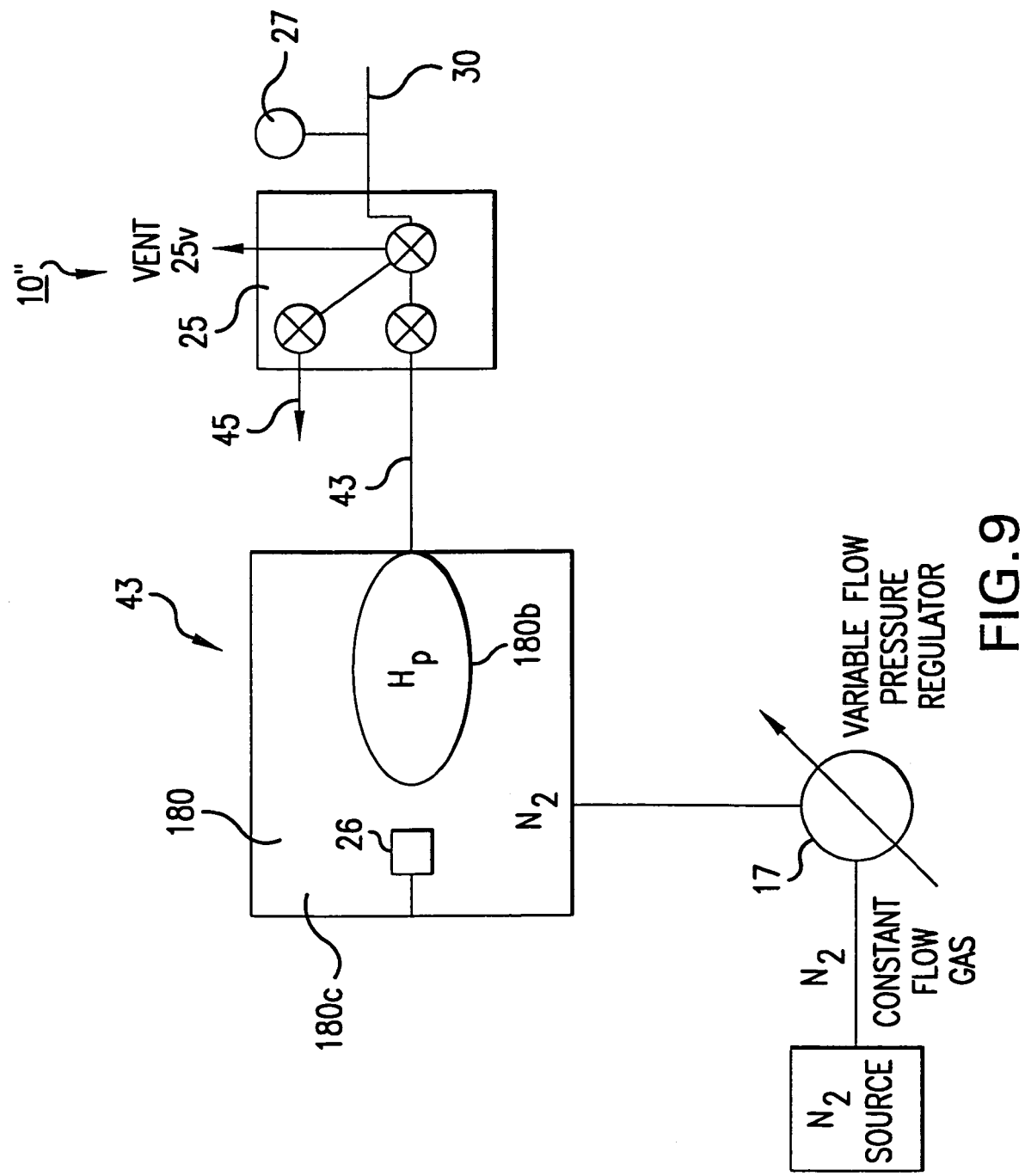
FIG. 9 is a schematic illustration of another alternative ventilator delivery system according to embodiments of the present invention.

FIG. 9 illustrates another embodiment of a ventilator system 10'' according to the present invention. This embodiment may be particularly suitable to dispense polarized gas or gas mixtures proximate in time (i.e., just prior or during) to MRI/NMR imaging or signal acquisition in a specified tidal volume operational mode. As shown, the polarized gas source 43 comprises a compressible container 180*b* inside a pressure vessel 180. In this embodiment, a constant flow of nitrogen is fed into a variable flow pressure regulator that controls the flow of the nitrogen into the vessel 180. The nitrogen in the vessel 180 compresses the container 180*b* that expels the hyperpolarized gas (Hp) to the gas delivery valve 25. A pressure sensor 26 is located in the container and measures the pressure Pc used to compress the container 180*b*. The PIP obtained from a normal breath (non-polarized gas) can be used as the pressure Pc adjusted by a constant or factor, as needed, based on the properties of the gas used to squeeze the bag. That is, nitrogen and air have similar properties, so the normal breath pressure may be used. However, helium is less dense and a correction factor of air to helium can be used to provide the desired pressure (e.g., X cc's of air=Y cc's of He). The tidal volume V$_T$ can be the same value as that calculated in a normal breath cycle.

In operation, the system 10'' applies pressure to the bag 180*b* by pressurizing the chamber 180*c* in the vessel 180. The chamber 180*c* can be pressurized to a pressure that is greater than the "current" PIP pressure (taken as a substantially real-time dynamic measurement). The pressure for the chamber 180*c* can be determined by multiplying the PIP times a constant adjustment factor to adjust for the difference in density and distance to the animal.

Figure 16:
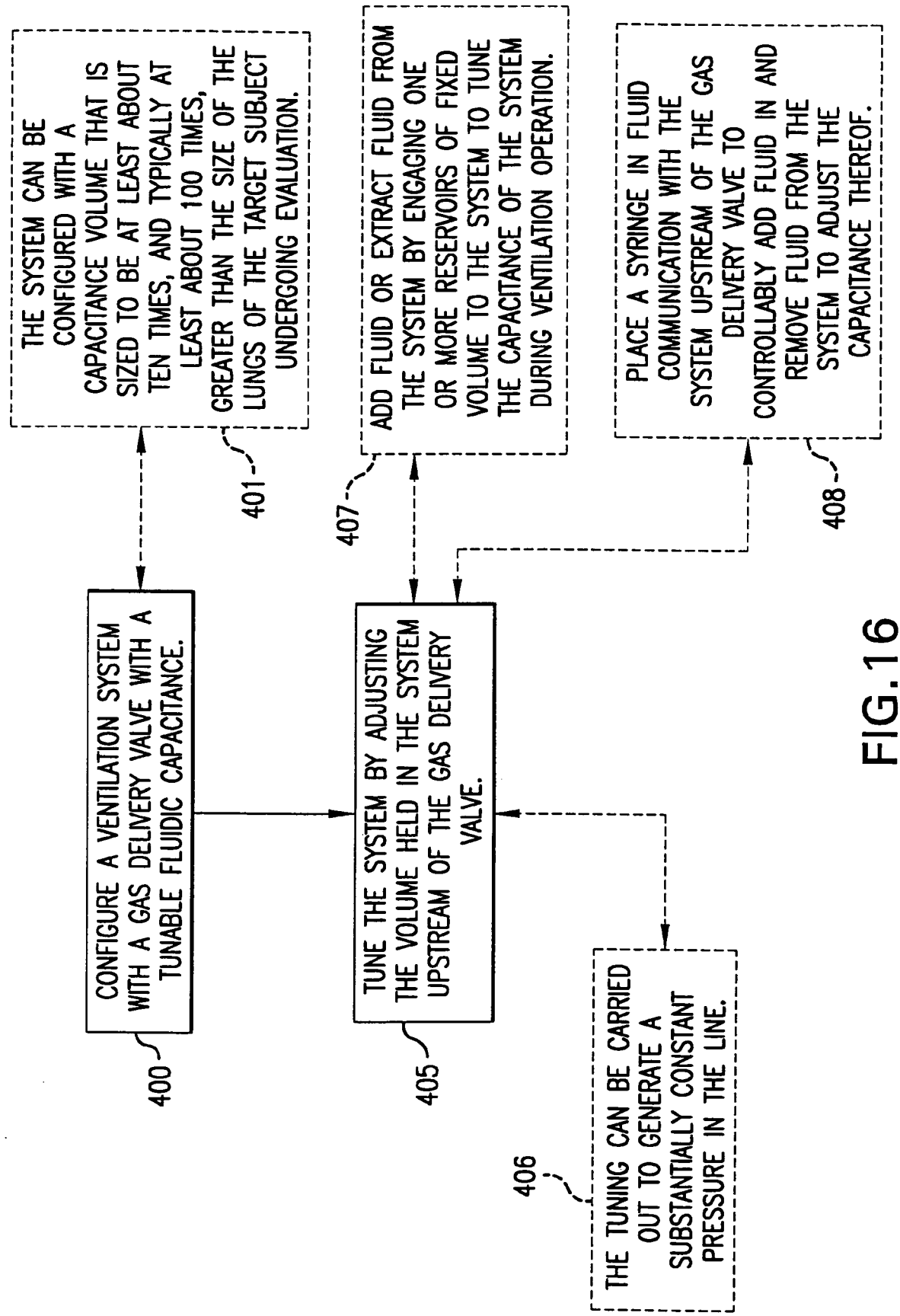
FIG. 16 is a block diagram of operations that can be used to dispense a selected gas during ventilation of a subject according to embodiments of the present invention.

FIG. 16 is a block diagram of operations that can be carried out to ventilate a subject according to embodiments of the present invention. As shown, a ventilation system can be configured with a gas delivery valve and a tunable fluidic capacitance (block 400). The system can be configured with an adjustable capacitance volume that is at least about three times, typically at least about ten times, and more typically at least about 100 times greater than the size of the lungs of the target subject undergoing evaluation (block 401). The capacitance size may be selected based on the average size of the lungs of the animal species undergoing evaluation. The system can be tuned by adjusting the volume of fluid held in the system manifold line upstream of the gas delivery valve (block 405).

The tuning can be carried out to maintain a substantially constant pressure (block 406). The increase and/or decrease in fluid can be carried out by selectively engaging-or disengaging one or more fixed volume lines or reservoirs (block 407) and/or by using a syringe that can inject and extract fluid from the system to adjust the capacitance.

Figure 10A:
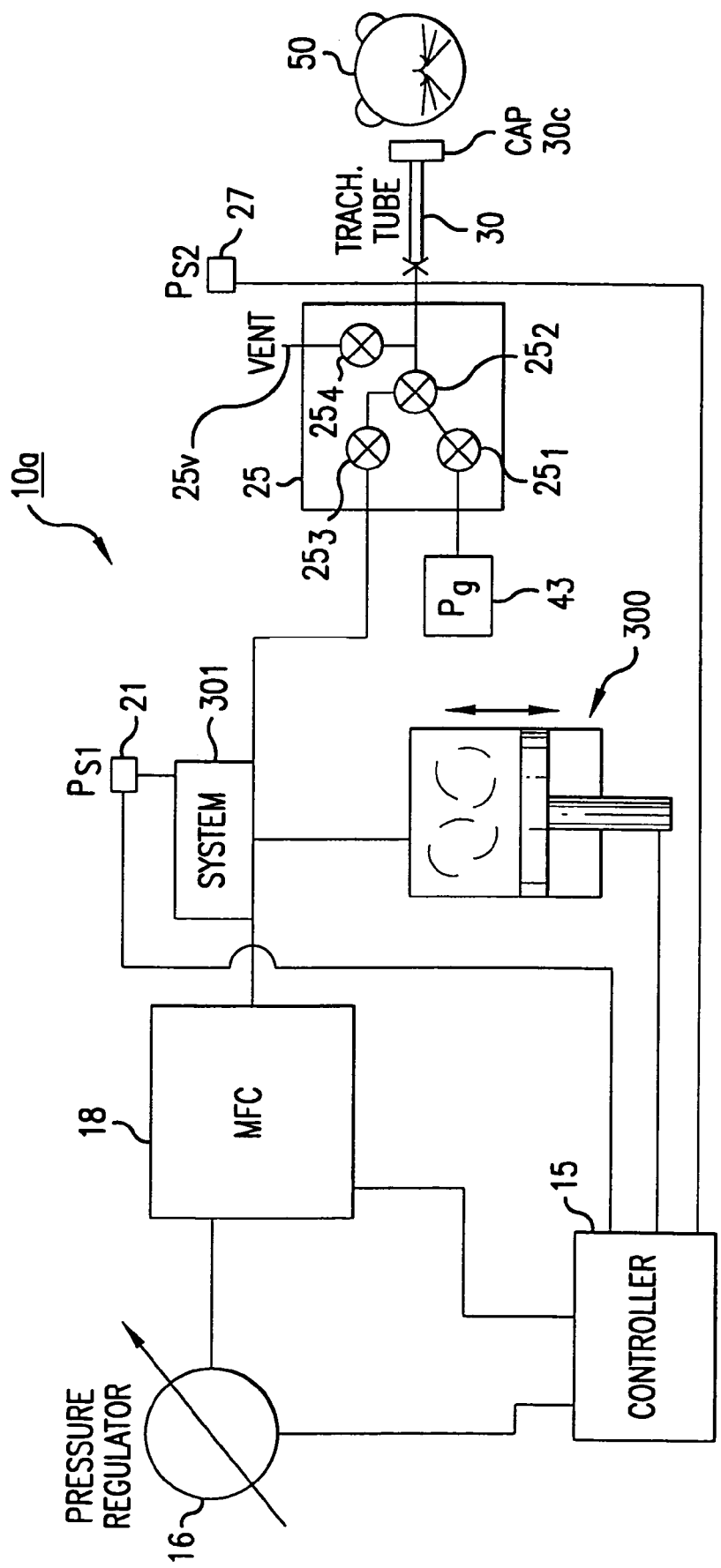
FIG. 10A is a schematic illustration of yet another ventilator delivery system according to embodiments of the present invention.

FIG. 10A illustrates one embodiment of a ventilator system 10*a* with a variable mass flow tuning system having a tunable capacitance "C" that can reduce pressure variations and even out the operational pressure of the system 10*a*. As shown, the system 10*a* is configured with an increased fluid volume 301 and a syringe 300 or other input/output fluid adjustment mechanism that can add and/or remove a desired controlled amount of fluid to tune the system and create a substantially constant pressure at the first sensor 21 (as shown in FIG. 5B). The capacitance volume may be between about 50-1500 ml. The system 10*a* can also include a pressure regulator 16 disposed upstream of the mass flow controller 18. The capacitance is defined by a fluid volume 301 upstream of the gas delivery valve 25. The capacitance can be at least ten times the volume of the lungs, and typically at least about 100 times greater than the volume of the lungs of the subject. Thus, for example, for a subject having a 3 ml lung capacity, the system 10*a* can be configured with a 300 ml fluid capacitance.

Figure 10B:
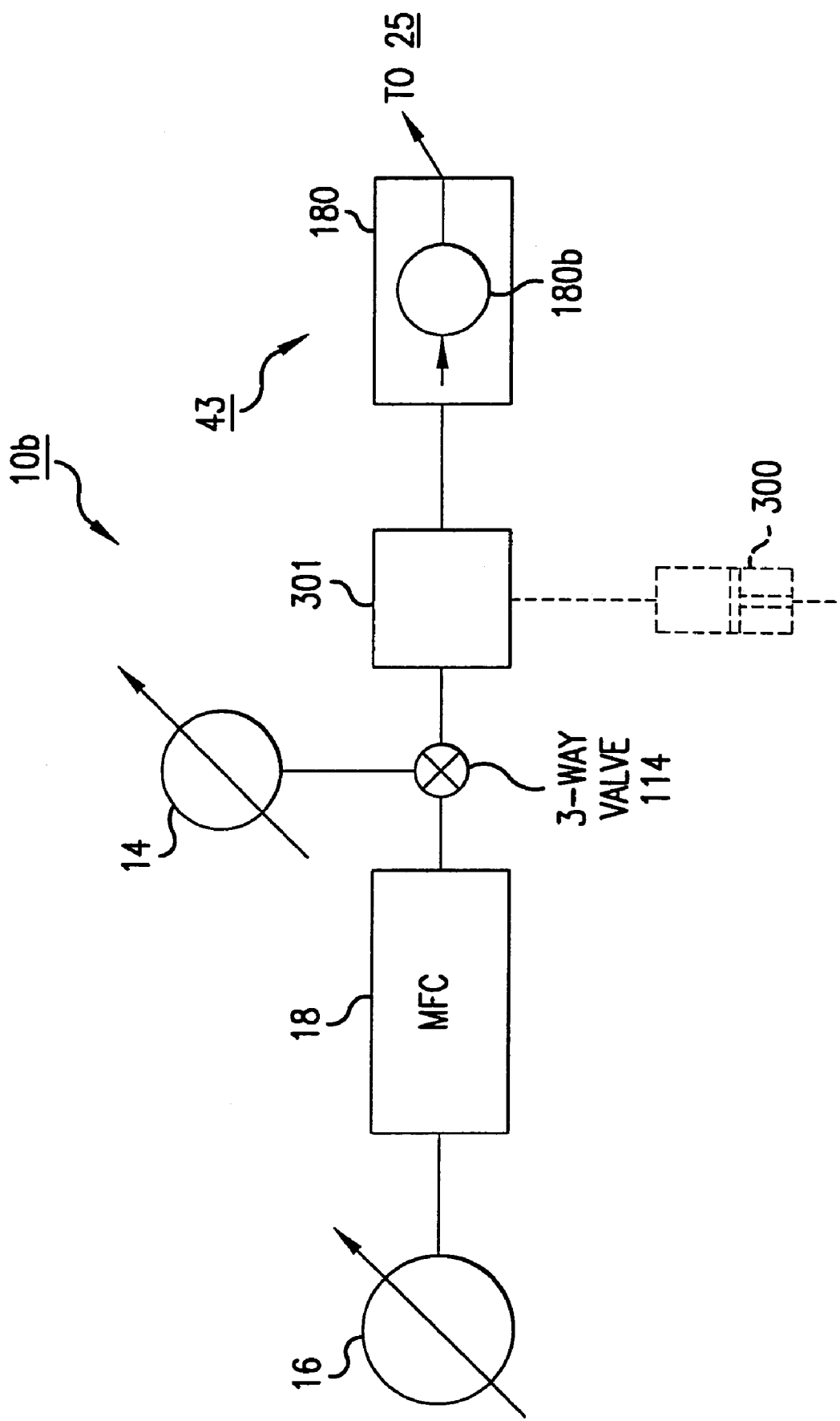
FIG. 10B is a schematic illustration of an additional ventilator delivery system according to embodiments of the present invention.

FIG. 10B illustrates another embodiment of a system 10*b*. In this embodiment, a three-way valve 114 can be positioned intermediate the mass flow controller 18 and polarized gas source 43. The system 10*b* can also include a pressure regulator 14 in communication with the three-way valve 114 and a pressure regulator 16 upstream of the mass flow controller 18. In operation, the three-way valve 114 is configured to temporarily disconnect the mass flow controller 18 when the system 10*b* is in the tidal volume dispensing mode (operating to dispense a selected predetermined tidal volume of hyperpolarized gas). The nitrogen pressure can be controlled or set by the pressure regulator 14 and reservoir or lump capacitance 301 (defined by one or more upstream reservoirs or fixed volumes (tied into the line in series or parallel) to keep the pressure substantially steady state during tidal volume dispensing of the polarized gas. The nitrogen at a controlled pressure is then directed into vessel 180 to compress the bag 180*b* of hyperpolarized gas. Examples of suitable bags are described in U.S. Pat. No. 6,423,387, the content of which is hereby incorporated by reference as if recited in full herein.

Figure 11:
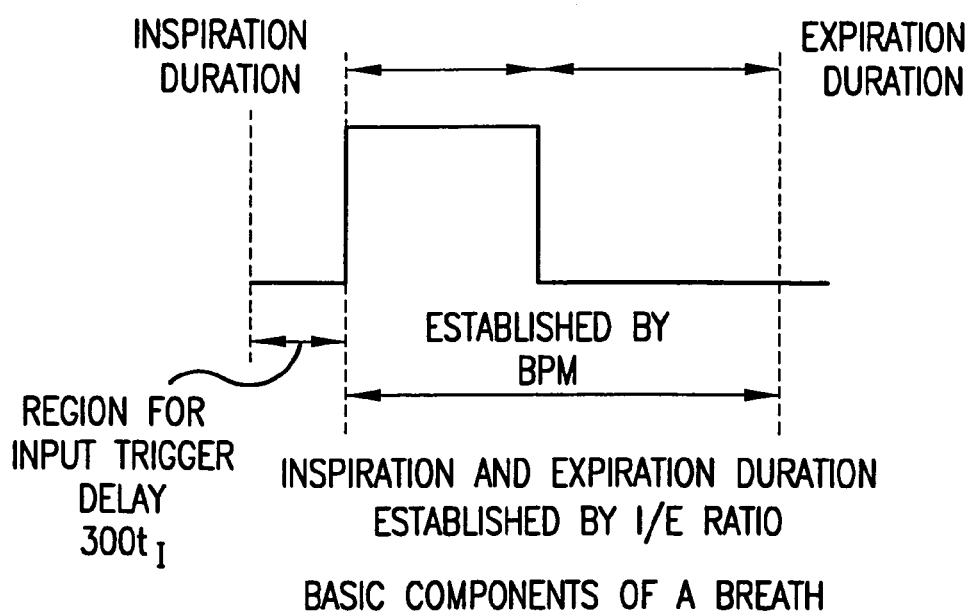
FIG. 11 is a timing diagram of inspiration and expiration that can be used in conjunction with embodiments of the present invention.
Figure 12:
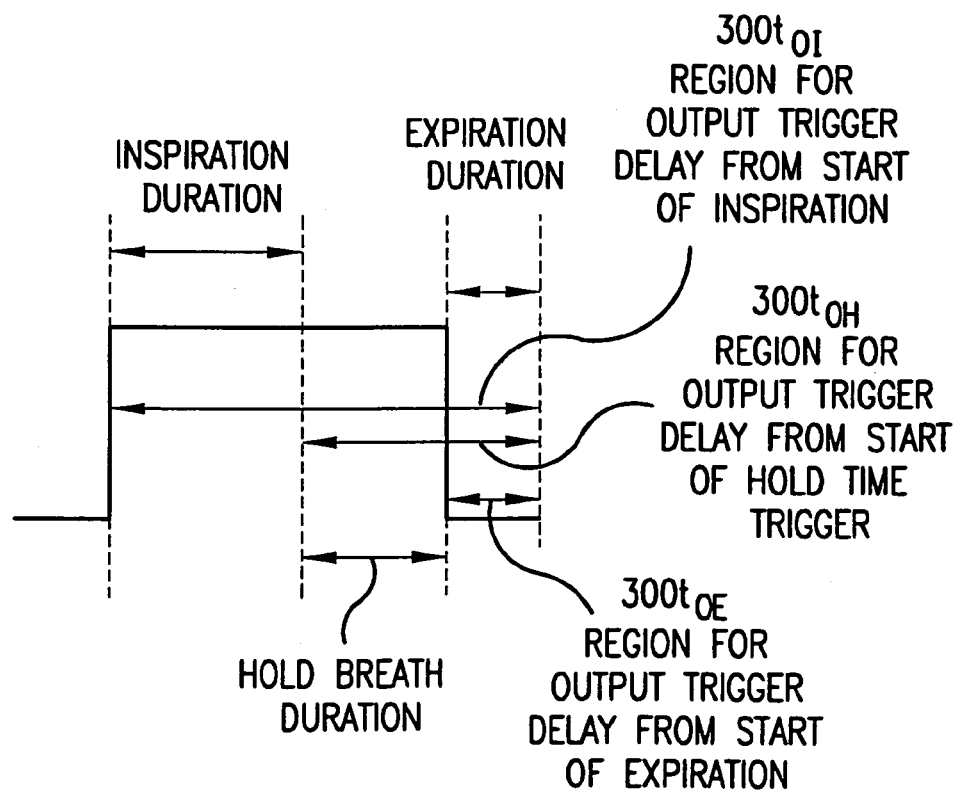
FIG. 12 is a timing diagram of a ventilation cycle with breath-hold and associated trigger regions that can be used in conjunction with embodiments of the present invention.

FIG. 11 illustrates the basic components of a breath cycle during ventilation. As shown, there is an inspiration and expiration duration that can be selected based on the I/E ratio. In the embodiment shown in FIG. 11, there is also a region for input trigger delay $300t_I$ (the trigger for obtaining an MRI/NMR signal) can be timed to start a predetermined delay period from this time in the cycle. FIG. 12 illustrates the breath cycle with a hold-breath portion and three potential regions for output trigger delays: an output trigger delay from the start of inspiration $300t_{OI}$; an output trigger delay from the start of breath hold time $300t_{OH}$; and an output trigger delay from the start of expiration $300t_{OE}$.

Figure 13:
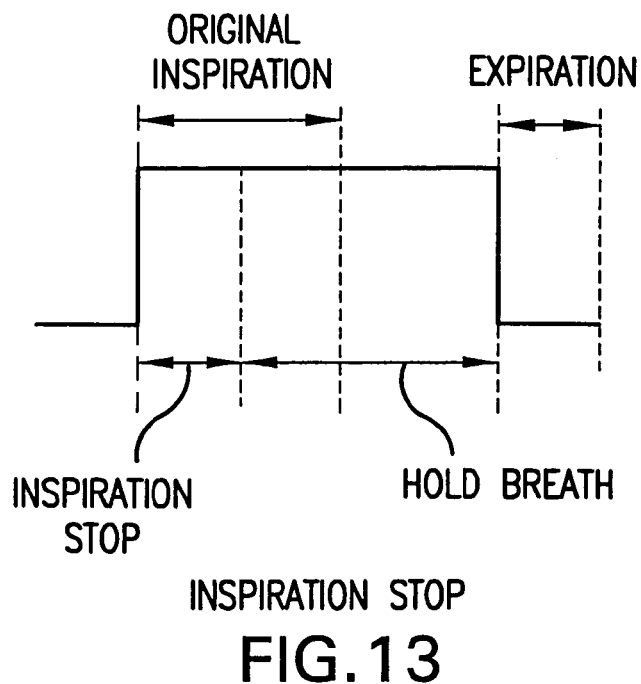
FIG. 13 is a timing diagram of inspiration stop in relation to the inspiration/expiration and breath-hold cycle according to embodiments of the present invention.
Figure 14:
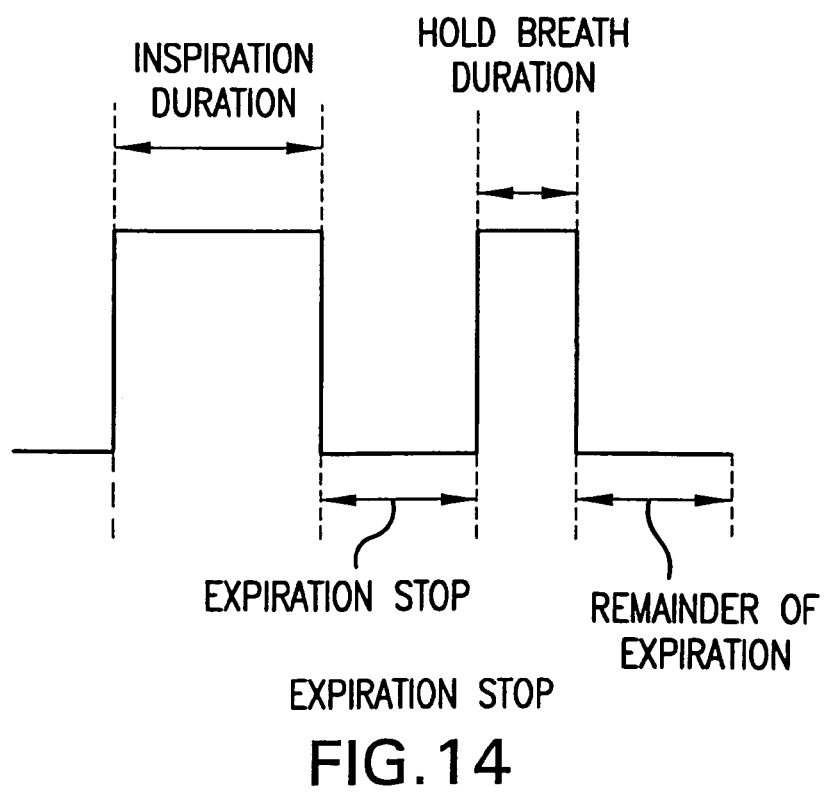
FIG. 14 is a timing diagram of expiration stop in relation to inspiration/expiration and breath-hold cycle according to embodiments of the present invention.

FIGS. 13 and 14 illustrate different portions of the breath cycle in which to initiate the breath-hold time of the polarized gas. FIG. 13 illustrates an inspiration stop and FIG. 14 illustrates an expiration stop.

FIG. 17 and FIGS. 17A-I illustrate an example of an automated ventilator system 10d according to certain embodiments of the present invention. As shown, the system 10d includes a gas control module 500 that may be configured to reside in a desktop enclosure. The gas control module 500 includes a breathing gas control system 510, a polarized gas control system 520, and a gas delivery valve 25 control system 530. The breathing gas control system 510 includes a first breathing gas input 500i with associated pressures sensors, valves, and regulators, as well as the mass flow controller 18 and first pressure sensor 21. As shown, the breathing gas control section 510 can also be in communication with an adjustable capacitance volume reservoir 301 (which can have a capacitance volume of between about 50-1500 ml, or even more, in certain embodiments). Optionally, the breathing gas control system 510 can also be in communication with an anesthetic vaporizer and/or scrubber. Small inner diameter conduit (typically about ⅛-1/16 of an inch) can be used to connect components. As is also shown, the breathing gas control system 510 can include an optional second breathing gas input $500i_2$.

The polarized gas control system 520 also includes pressure regulators, pressure sensors, and valves that are in communication with the polarized gas source 43. The polarized gas source 43 is, in turn, in communication with the gas delivery valve 25 via small inner diameter polarization friendly tubing (shown as 1/16 inch i.d. tubing).

The gas delivery valve 25 control system 530 includes a pressure regulator and pressure transducer and a series of valves that control inhale, exhale and gas output to the subject. The configuration shown contemplates the use of a diaphragm valve 25, but as noted above, other gas delivery valve 25 configurations can be used and the gas delivery valve control system 530 modified accordingly. In certain embodiments, such as where pressure transients may be undesirable and/or problematic, orifices can be added to the transducer lines (not shown).

The control module 500 can be configured to be in communication with various components and peripheral devices. As shown, the system 10d can include a vital signs/power supply module 550 that may also be provided in the desktop enclosure housing the control module 500. The vital signs/power supply module 550 can include a blood pressure sub-module 552 that communicate with a blood pressure sensor 550s, a cardiotachometer sub-module 553 that communicates with a heart monitoring sensor 550s, and a gas pressure sub-module 551. The system 10d can also include a blanket-type heating pad 560 with temperature controller 570. The system 10d can also include an optional $CO_2$ analyzer $575_1$ and/or scrubber $575_2$ connected to vent port 25v of the valve 25. As shown by the designation 600 and software control box, the system 10d can be software controlled for automated operation.

Figure 17:
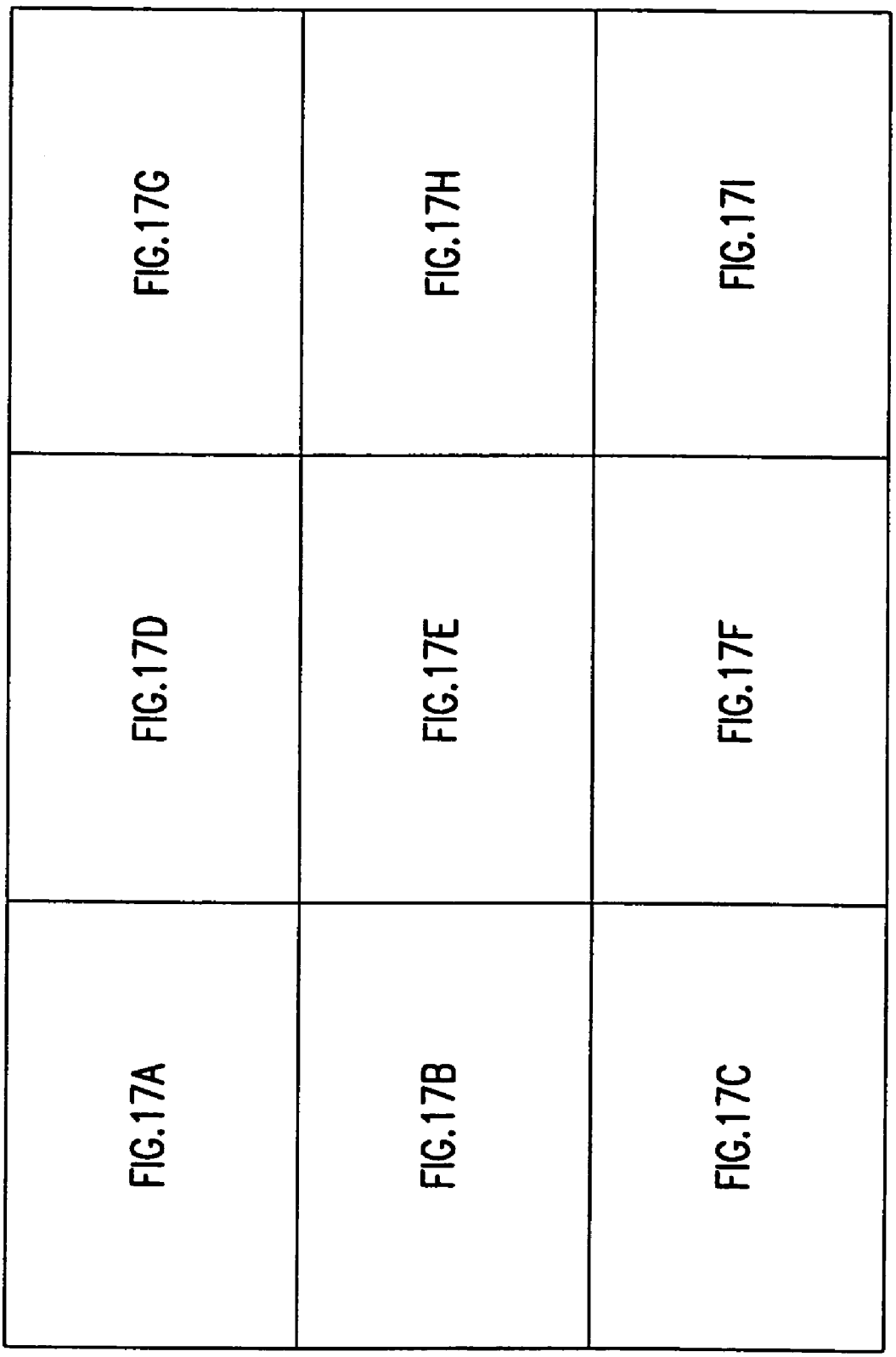
FIG. 17 illustrates how
Figure 17A:
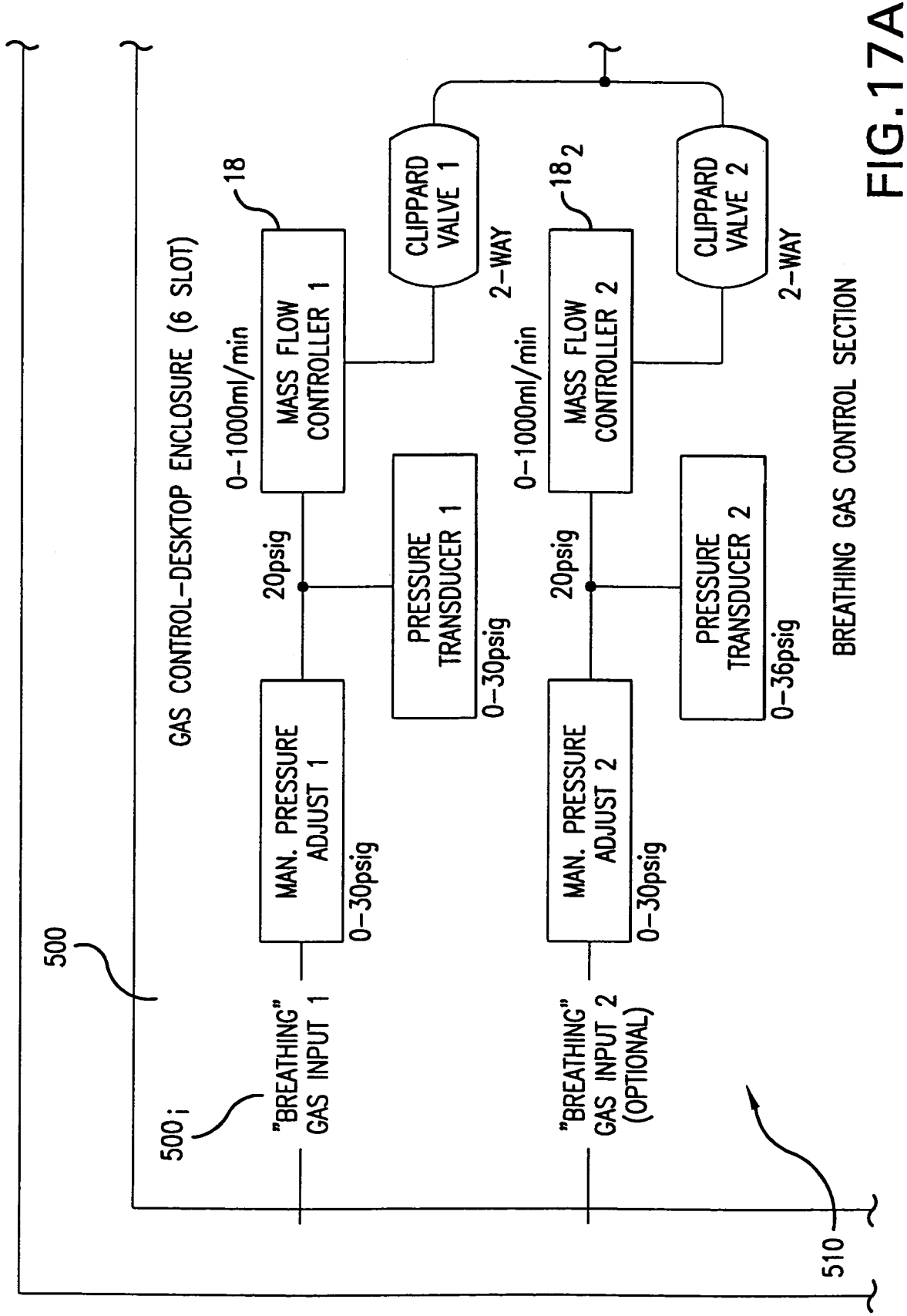
Figure 17B:
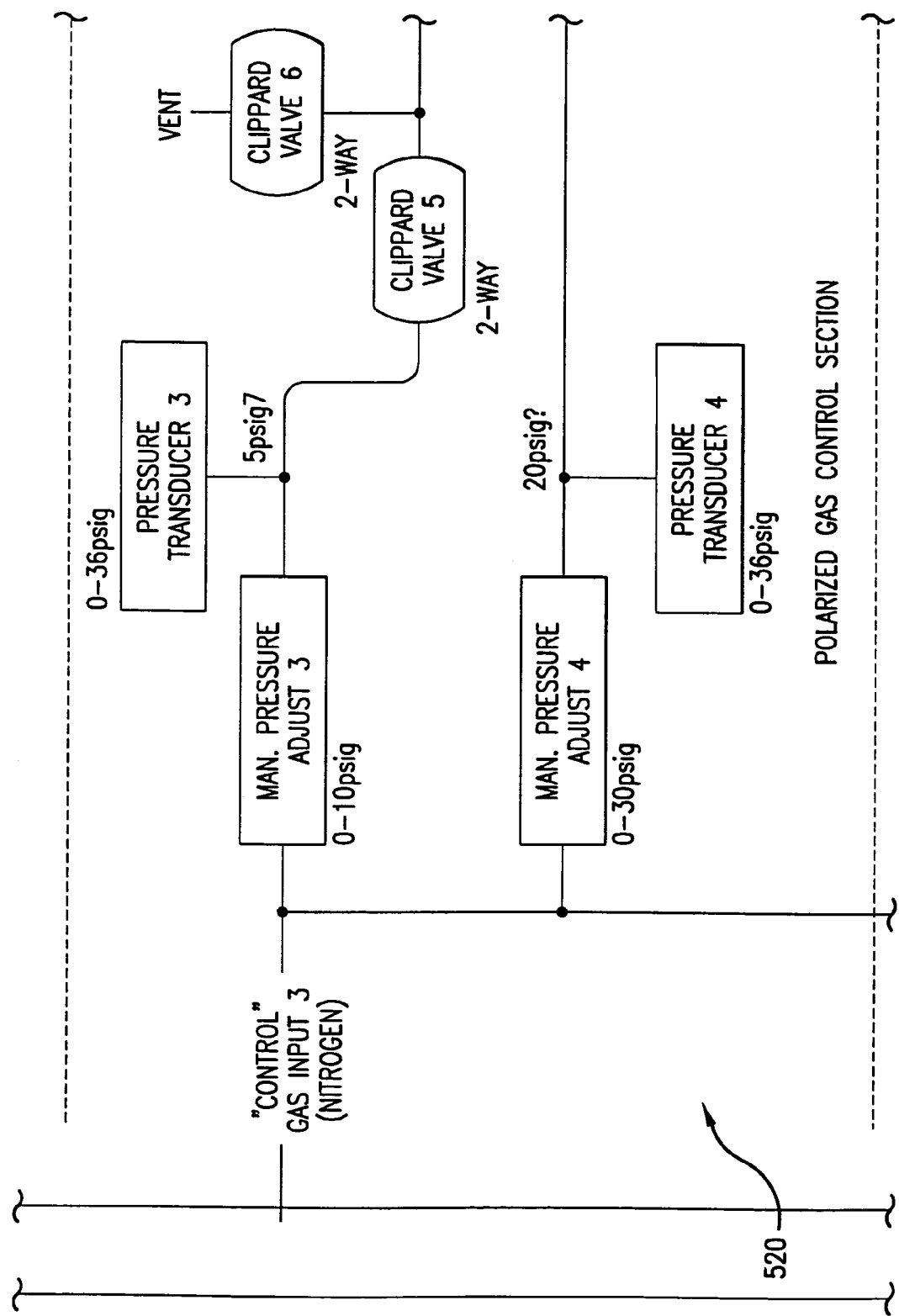
Figure 17C:
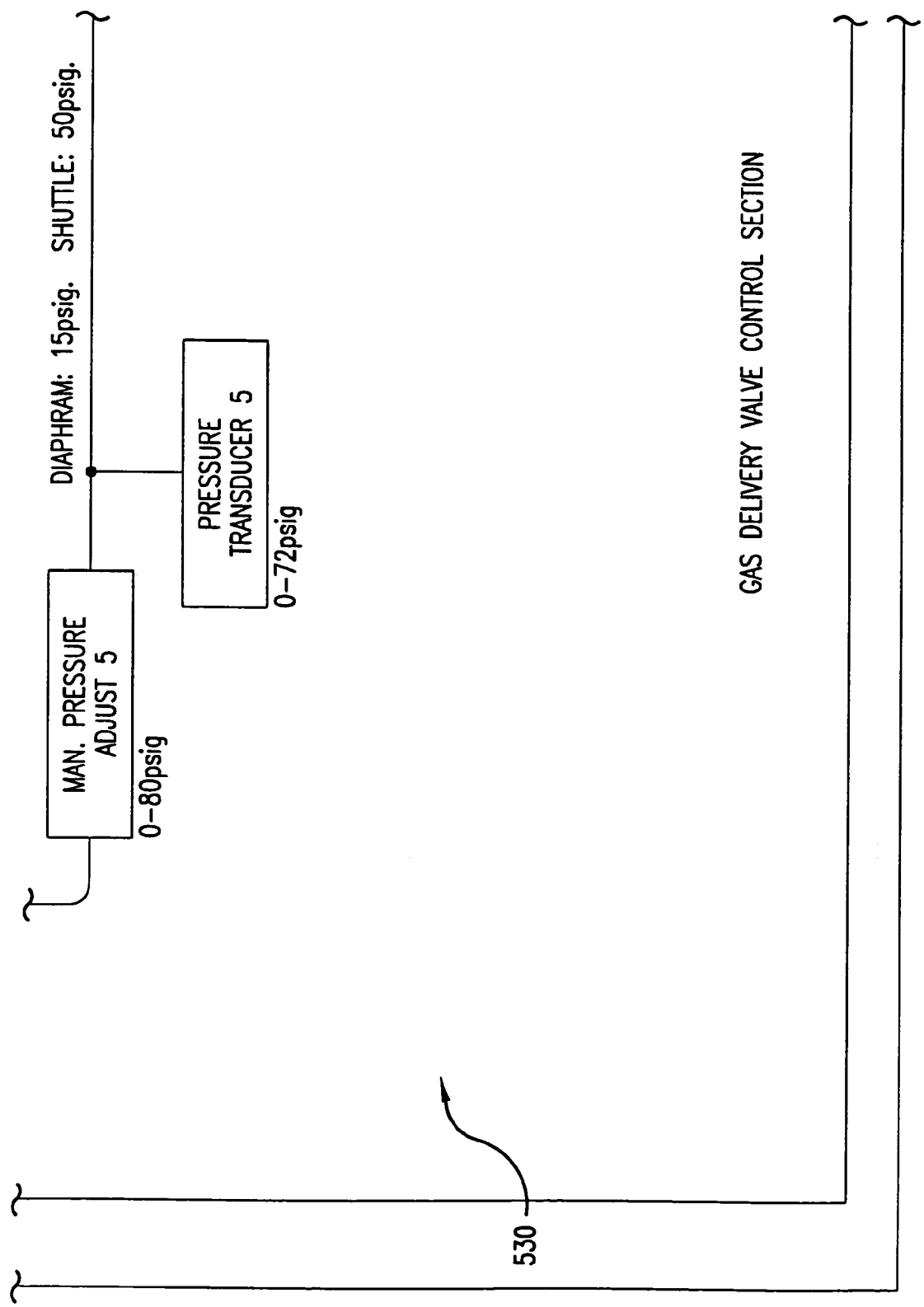
Figure 17D:
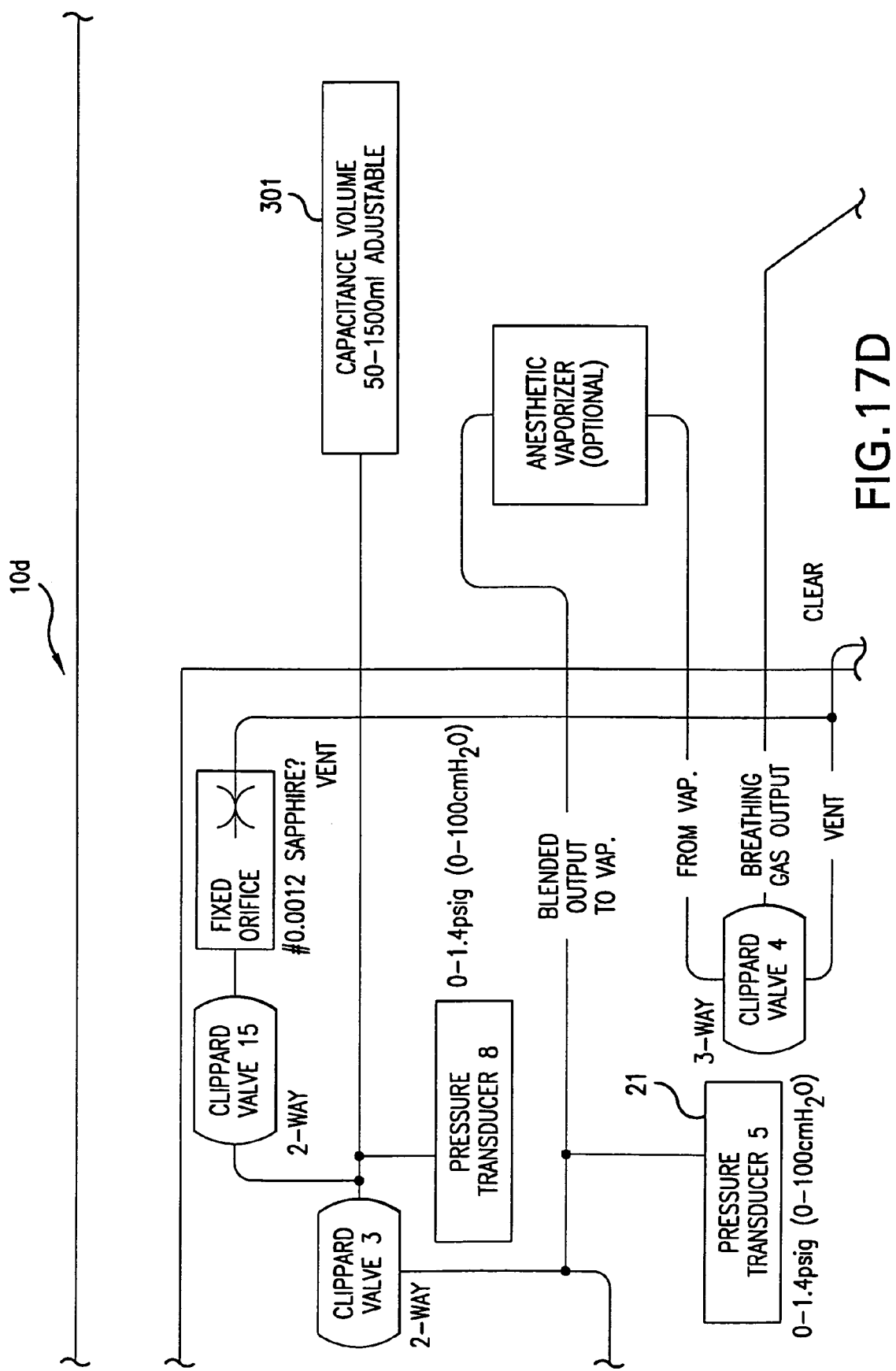
Figure 17E:
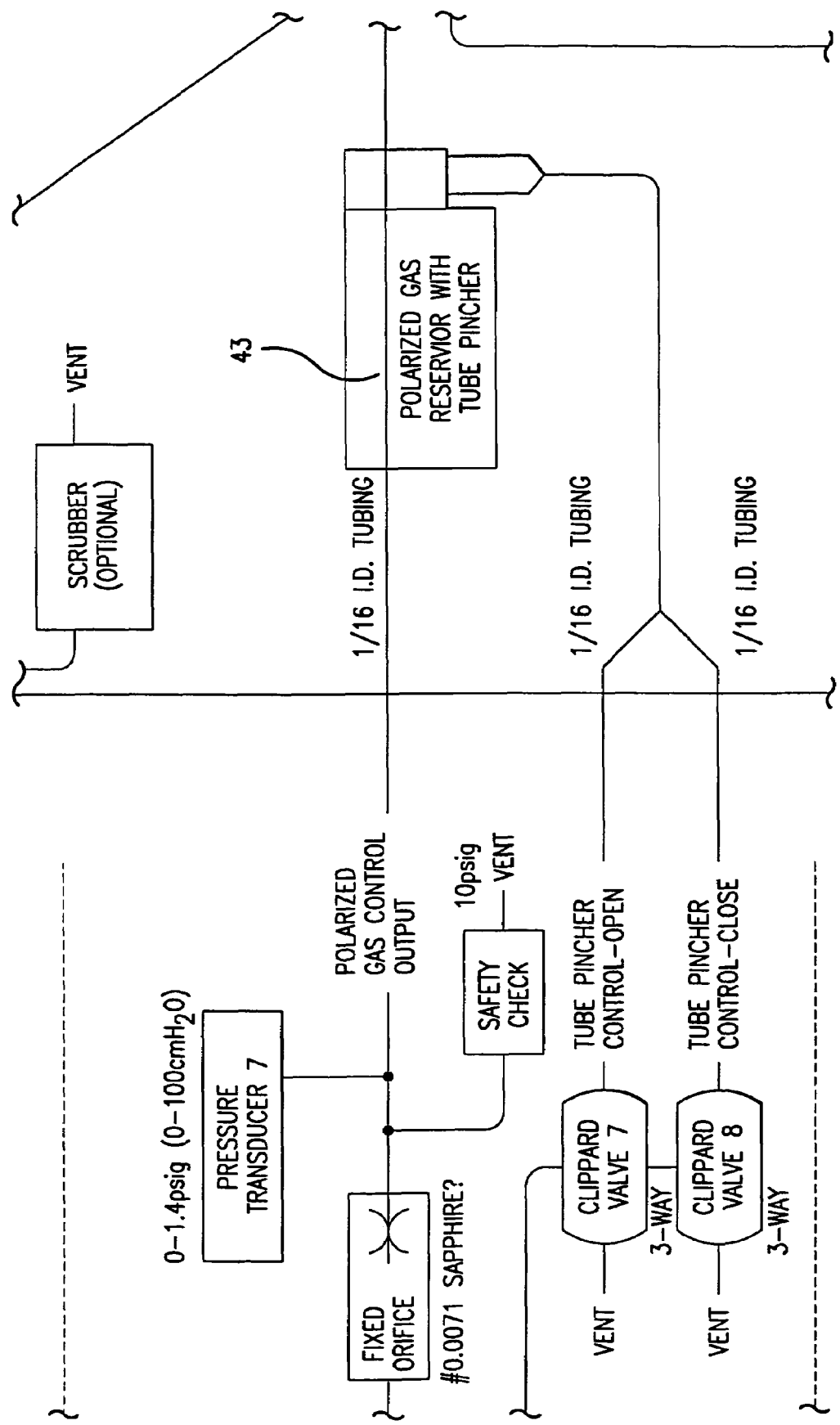
Figure 17F:
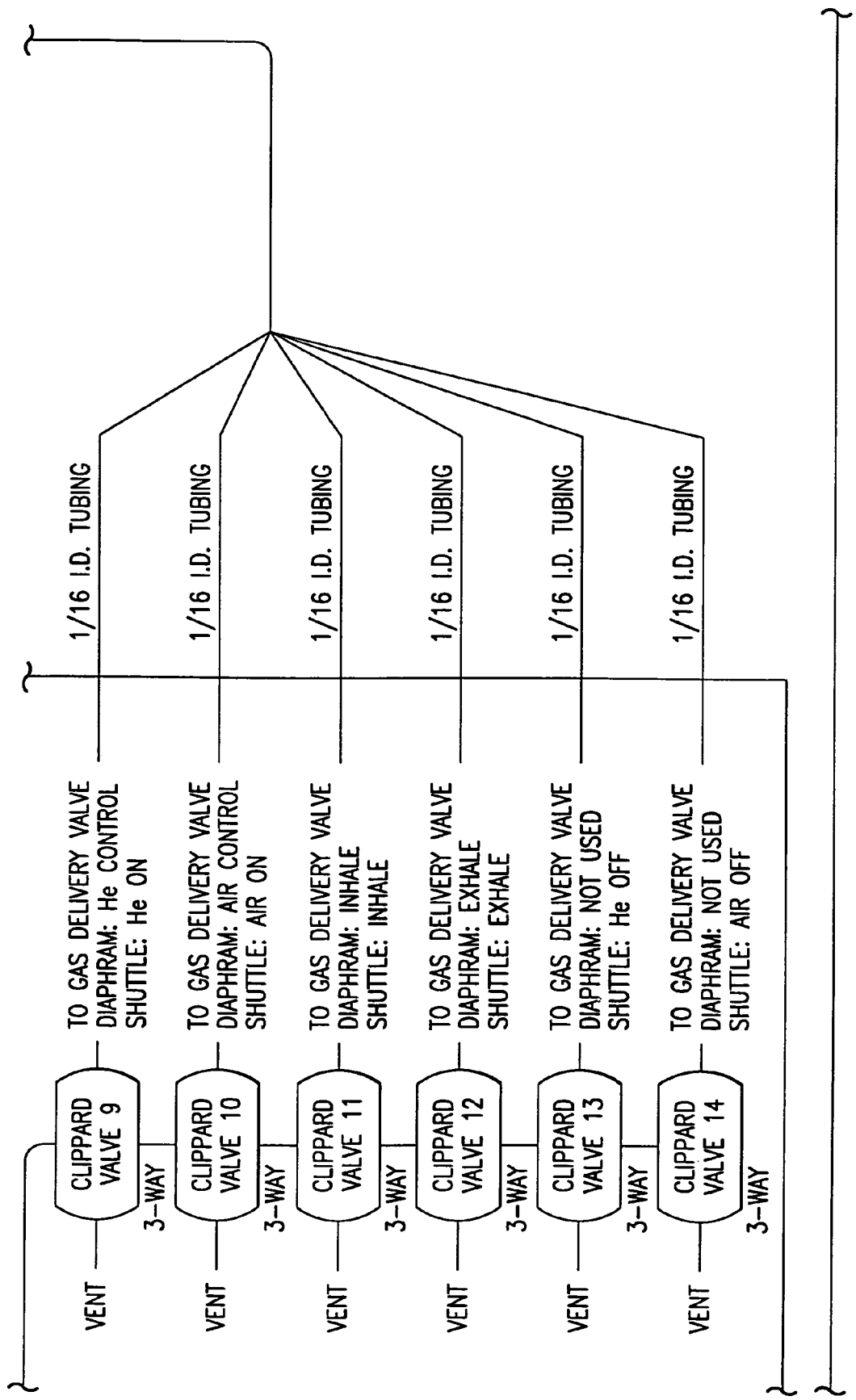
Figure 17H:
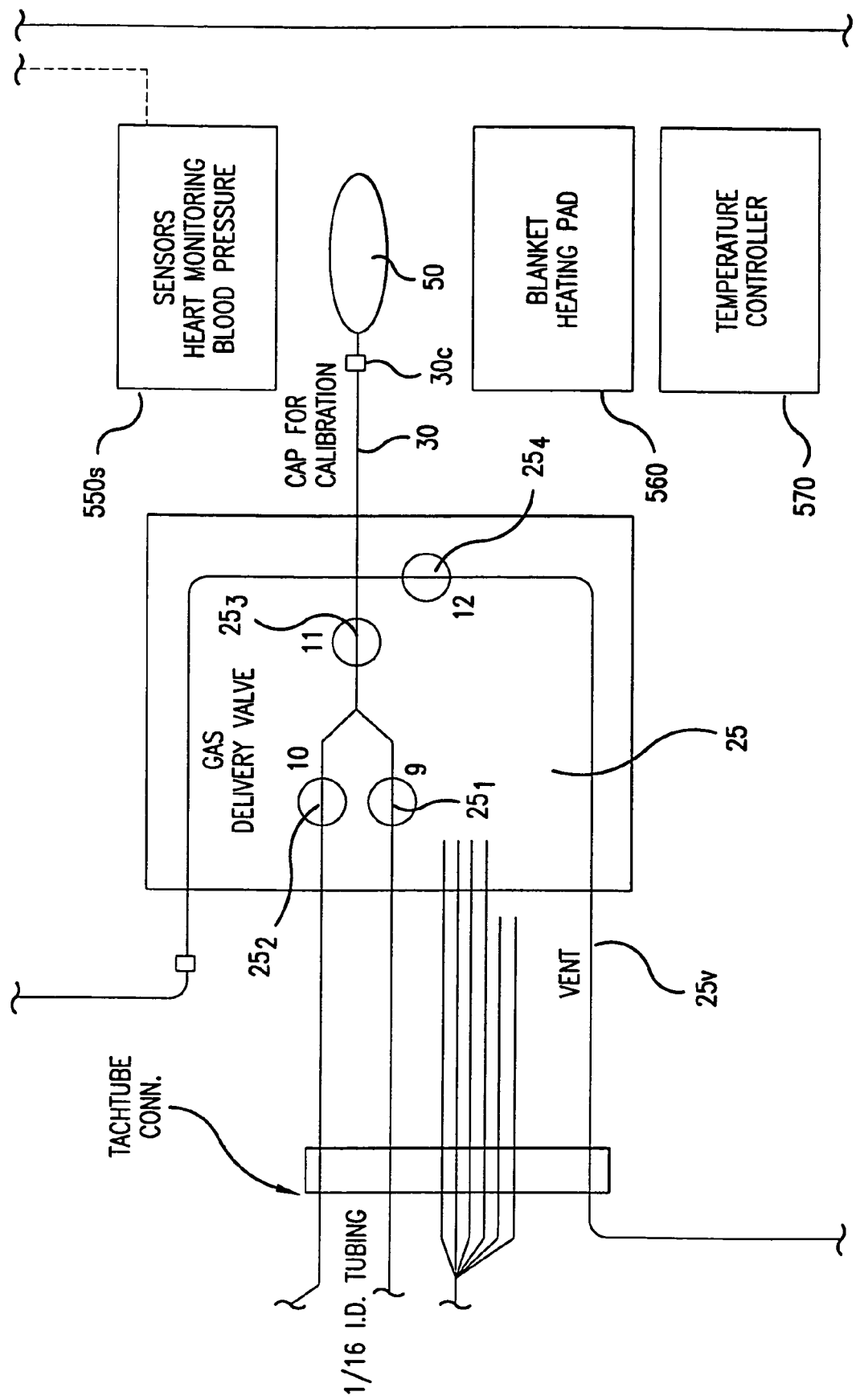
Figure 17I:
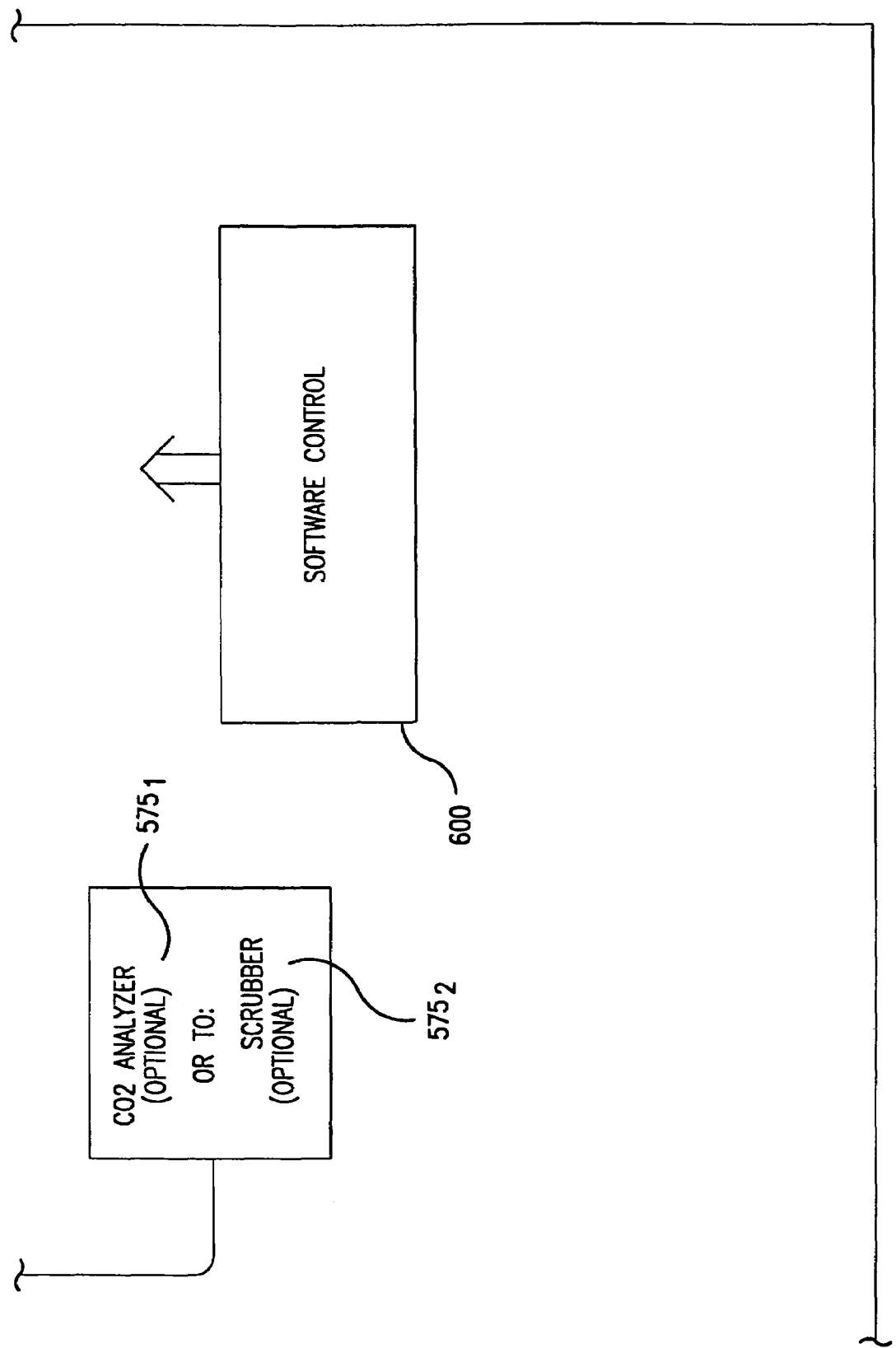

In certain embodiments, as shown in FIG. 17A, the system can employ two mass flow controllers 18 and $18_2$. The mass flow controllers can be used to blend standard ventilation gases (such as oxygen and air) during non-polarized gas ventilation. The system can be configured to automatically control the operation of the supplemental mass flow controller to deliver a desired blend, mix or concentration of gases to the subject (such as to supply about 30% oxygen with 70% air).

It is noted that the features described above with respect to one embodiment of a ventilator described herein may be applied to other embodiments.

As will be appreciated by one of skill in the art, the present invention may be embodied as a method, data or signal processing system, or computer program product. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, or C++. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user=s computer and partly on a remote computer or entirely on the remote computer. In the latter scenario, the remote computer may be connected to the user=s computer through a local area network (LAN) or a wide area network (WAN), or the connection may be made to an external computer (for example, through the Internet using an Internet Service Provider).

Figure 15:
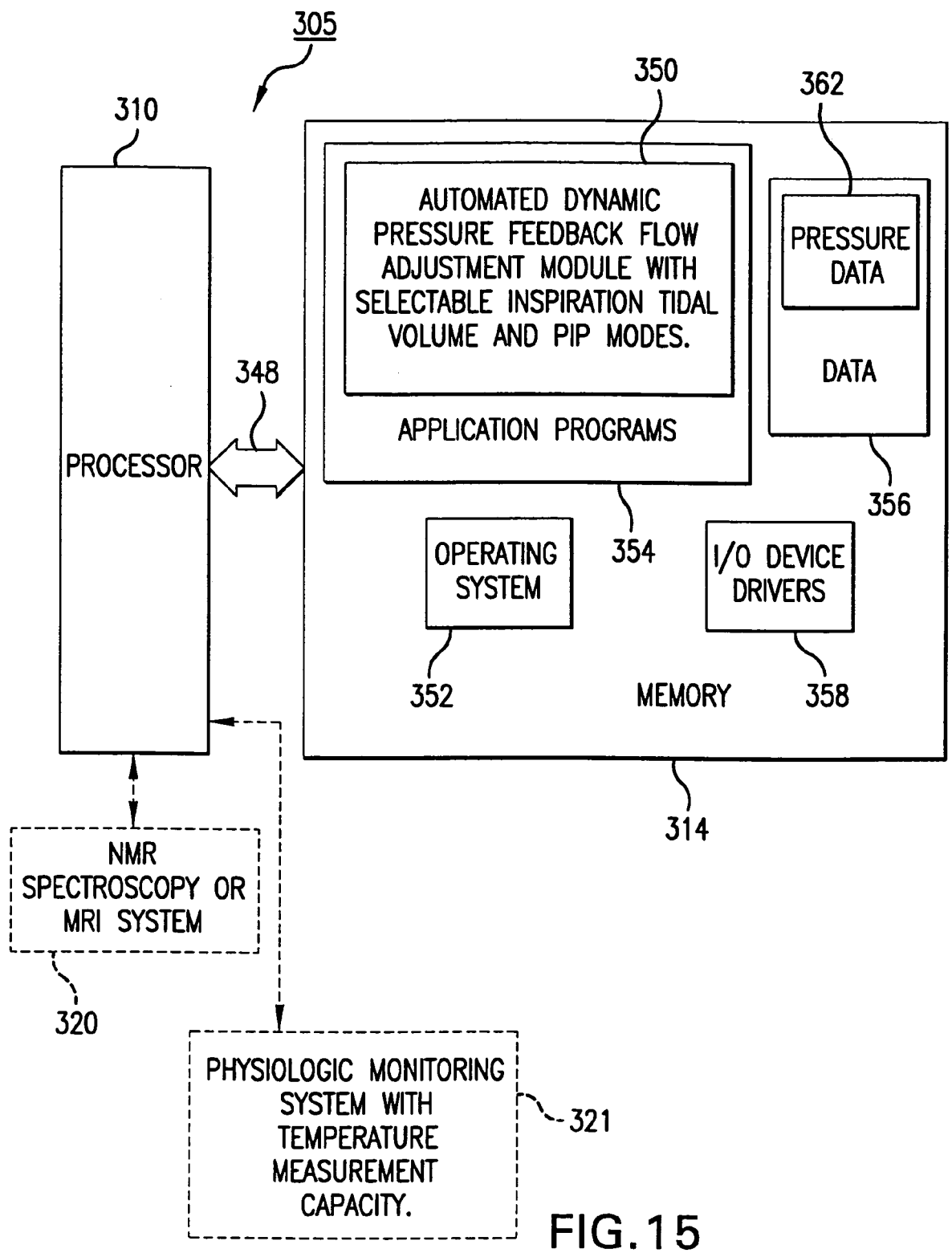
FIG. 15 is a block diagram of an automated dynamic pressure feedback system for controlling tidal volume or inspiration pressure for delivering hyperpolarized gas using a ventilator system according to embodiments of the present invention.

FIG. 15 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 15, the memory 314 may include several categories of software and data used in the data processing system 305: the operating system 352; the application programs 354; the input/output (I/O) device drivers 358; an automated dynamic pressure feedback flow adjustment module with selectable inspiration tidal volume and PIP operational modes 350; and the data 356.

The data 356 may include ventilation system operational data 362 which may be obtained from the ventilation system, patient physiological data, and/or may be NMR/MRI data from an NMR spectroscopy or MRI system 320. As will be appreciated by those of skill in the art, the operating system 352 may be any operating system suitable for use with a data processing system, such as OS/2, AIX or OS/390 from International Business Machines Corporation, Armonk, N.Y., WindowsXP, WindowsCE, WindowsNT, Windows95, Windows98 or Windows2000 from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and preferably include at least one application that supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Feedback Module 350 being an application program in FIG. 15, as will be appreciated by those of skill in the art, other configurations may also be utilized while still benefiting from the teachings of the present invention. For example, the Pressure Feedback Module 350 may also be incorporated into the operating system 352, the I/O device drivers 358 or other such logical division of the data processing system 305. Thus, the present invention should not be construed as limited to the configuration of FIG. 15, which is intended to encompass any configuration capable of carrying out the operations described herein.

In certain embodiments, the Pressure Feedback Module 350 includes computer program code for timing the delivery of the desired inhalation gas(es) and may include code for tracking polarization level data of the dispensed hyperpolarized gas. The Module 350 can direct initiation of operations that will automatically sequence the system to output at a desired breath per minute rate, a desired I/E ratio, a target breath-hold time and may automatically adjust the pressure in the system based on sensed pressures.

The I/O data port can be used to trigger NMR/MRI signal acquisition and/or to transfer information between the data processing system 305 and the NMR/MRI data acquisition system 320 or another computer system, a network (e.g., the Internet) or other device controlled by the processor. These components may be conventional components such as those used in many conventional data processing systems, which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 15 but is intended to encompass any configuration capable of carrying out the operations described herein.

The flowcharts and block diagrams of certain of the figures herein illustrate the architecture, functionality, and operation of possible implementations of probe cell estimation means according to the present invention. In this regard, each block in the flow charts or block diagrams represents a module, segment, or portion of code, which comprises one or more executable instructions for implementing the specified logical function(s). Certain of the flowcharts and block diagrams illustrate methods to operate hyperpolarizers or components thereof to yield polarized gas according to embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

As noted above, the systems 10, 10', 10", 10a, 10b can be configured to operate on the theory of flow into the system is equal to the flow out of the system. The following non-limiting example is provided in further description of the present invention.

EXAMPLE

The following exemplary listing of sequence of operations can be used to deliver gas from the ventilator.

1.1) Fixed Volume Calculation:

1.1.1) The fixed volume of the system from the inhale port to the animal connection point including the pressure transducer is calculated. This calculation may be conducted either through an automate sequence using the mass flow controller and the pressure transducers or using volumetric calculations and the known tube lengths and diameters.

1.1.2) An automated sequence may comprise the following steps:

1.1.2.1) Prompting/instructing the user to cap off the tubing at the animal connection point.

1.1.2.2) Prompting the user for the type of subject (animal) to be ventilated.

1.1.2.3) Setting the inspiration/expiration ratio to 50%.

1.1.2.4) Setting the BPM and the PIP to the pre-programmed system defaults for the animal being ventilated.

1.1.2.5) Instructing the system to flow at the default flow rate for the animal selected.

1.1.2.6) Adjusting the flow rate until the pressure read by PT1 substantially matches the pressure read by PT2 within a predetermined tolerance.

1.2) Once a steady state pressure is achieved, the volume is determined as follows:

$$\text{Fixed Volume} = Vcal = FR/(BPM((PT8/1033.51 \text{ cm H}_2\text{O}) + 1 \text{ ATM})).$$

Where FR=Flow rate.

1.3) Normal Breathing Gas Delivery:
1.3.1) User enters the animal type into an input device associated with the ventilator system (computer touch screen, keyboard and the like)
1.3.2) User enters in either a desired PIP or Tidal Volume ($V_T$).
1.3.3) User enters in a desired inspiration/expiration ratio.
1.3.4) User enters in a desired BPM.

Note, a default setting for each of the selectable parameters for a particular animal and/or size of animal can be programmed.

1.3.5) In PIP mode: (Note PIP is read at PT2)
1.3.5.1) The system calculates a starting Flow Rate (FR) based on the calibrated volume Vcal. This calculation can be based on $FR_{total} = FR_{cal} + FR_{animal}$; where $FR_{cal}$ is the amount of flow used to raise the fixed volume from 1 ATM to the desired PIP and $FR_{animal}$ is the flow rate used to deliver the default tidal volume to the animal at the desired PIP.
1.3.5.2) Initial flow rate can be established or estimated by:

$$FR_{cal} = BPM * (((1 + (PIP_{desired}/1033.51 \text{ cm } H_2O))*Vcal \quad 1.3.5.2.1)$$

$$FR_{animal} = BPM * V_{Tdefault}. \quad 1.3.5.2.2)$$

$$FR_{total} = FR_{cal} + FR_{animal}. \quad 1.3.5.2.3)$$

1.3.5.3) Flow can then be initiated.
1.3.5.3.1) If the $PIP_{read} < PIP_{desired}$ then the FR can be (incrementally) increased until the desired PIP is reached.
1.3.5.3.2) PIP can be based on a plurality of cycles, typically an average of 5 contiguous cycles.
1.3.5.3.3) If $PIP_{read} > PIP_{desired}$ then FR can be incrementally decreased until the $PIP_{desired}$ is reached.
1.3.5.3.4) If $PIP_{desired}$ cannot be reached then an error can be indicated to the user.
1.3.5.4) After the PIP reading has stabilized:
1.3.5.4.1) PIP shall be the stabilized reading in cm $H_2O$.
1.3.5.4.2) The tidal volume shall then be calculated:

$$V_T = V_{Total} - V_{fixed}. \quad 1.3.5.4.2.1)$$

$$V_{fixed} = V_{cal} * ((PIP_{read}/1033.51 \text{ cm } H_2O) + 1). \quad 1.3.5.4.2.2)$$

$$V_{Total} = FR/BPM * ((PIP_{read}/1033.51 \text{ cm } H_2O) + 1). \quad 1.3.5.4.2.3)$$

1.3.5.4.3) Once the tidal volume has been calculated it can be tested to see if it is within the minimum ($V_{Tmin}$) and maximum ($V_{Tmax}$) range for the animal being ventilated.
1.3.5.4.4) If $V_T < V_{Tmin}$ then the $PIP_{desired}$ shall be increased and an error message can be sent to the user.
1.3.5.4.5) If $V_T > V_{Tmin}$ then the $PIP_{desired}$ shall be decreased and an error message can be sent to the user.

1.3.6) In $V_T$ mode:
1.3.6.1) The system can calculate a starting FR based on the desired $V_T$ entered by the user.

$$FR_{total} = FR_{cal} + FR_{animal}. \quad 1.3.6.1.1)$$

$$FR_{animal} = BPM * V_{Tdesired}. \quad 1.3.6.1.2)$$

$$FR_{cal} = BPM * (((1 + (PIP_{default}/1033.51 \text{ cm } H_2O)) * V_{cal}. \quad 1.3.6.1.3)$$

1.3.6.2) The $V_T$ can be calculated each time the PIP stabilizes.

$$V_T = V_{Total} - V_{fixed}. \quad 1.3.6.2.1)$$

$$V_{fixed} = V_{cal} * ((PIP_{read}/1033.51 \text{ cm } H_2O) + 1). \quad 1.3.6.2.2)$$

$$V_{Total} = FR/BPM * ((PIP_{read}/1033.51 \text{ cm } H_2O) + 1). \quad 1.3.6.2.3)$$

1.3.6.3) If $V_T$ is $< VT_{desired}$ then $PIP_{desired}$ can be increased.
1.3.6.4) If $V_T$ is $> VT_{desired}$ then $PIP_{desired}$ can be decreased.
1.3.6.5) The PIP can be tested to see if it is outside the minimum PIP ($PIP_{min}$) and maximum PIP ($PIP_{max}$) for the animal being imaged.
1.3.6.5.1) If the $PIP_{min} \leq PIP_{read} \leq PIP_{max}$, then no fault message is generated and the new value can be utilized.
1.3.6.5.2) If the $PIP_{read}$ is $< PIP_{min}$ then the PIP is raised and an error message can be displayed to the user.
1.3.6.5.3) If the $PIP_{read} > PIP_{max}$, then the PIP is lowered and an error message can be displayed to the user.
1.3.6.6) Changing the PIP value will cause the computer program or software to change the FR setpoint.
1.3.6.7) Once the desired $V_T$ is reached the PIP will be $PIP_{read}$.

1.4) Imaging Gas Breathing:
1.4.1) The PIP from the normal breath analysis can be used as the pressure to squeeze the polarized gas source.
1.4.2) The $T_V$ can be presumed to be the same as that calculated in the normal breath cycle.
1.4.3) The actual pressure to the bag can be adjusted by a constant factor based on the properties of the gas being used to squeeze the bag.

In summary, the ventilation systems of the present invention allow for computer control and adjustment of the tidal volume and peak inspiration pressure delivered to the animal. The systems can also be configured to allow for data feedback from both sides of the gas delivery valve(s) and utilizes this feedback to make automated adjustments during operation of the device. The systems can include a mass flow controller so that the mole concentration to the animal can be determined.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of delivering hyperpolarized gas to a subject, comprising:
providing a ventilator system with a mass flow controller, a tracheal tube and a gas delivery valve configured to deliver hyperpolarized gas and at least one non-polarized gas to a subject;
monitoring a first pressure in the ventilator system upstream of the gas delivery valve;
monitoring a second pressure in the ventilator system downstream of the gas delivery valve;
obtaining a reading of the mass flow controller when the first pressure is substantially constant; and automatically determining the tidal inspiration volume of hyperpolarized gas delivered to the subject in situ using the obtained mass flow controller reading.

2. A method according to claim 1, wherein the ventilator system includes a variable flow rate mass flow controller disposed upstream of the gas delivery valve, said method further comprising automatically dynamically adjusting the flow rate of the mass flow controller to maintain a substantially constant first pressure during ventilation delivery of the hyperpolarized gas to the subject.

3. A method according to claim 1, further comprising accepting user input to select a tidal volume operational mode with the desired tidal volume selected or a peak inspiration pressure operational mode with the desired peak inspiration pressure selected.

4. A method according to claim 1, further comprising determining a fixed geometric volume based on pressure measurements taken while a distal end portion of the tracheal tube is closed, and subtracting the fixed geometric volume from the determined tidal volume.

5. A method according to claim 4, wherein the fixed geometric volume is determined for each size tracheal tubes used with the ventilator and/or for eacg species of subjects undergoing ventilation.

6. A method according to claim 1, further comprising selecting a desired ventilation delivery cycle with a breath per minute rate, a breath-hold duration and an inspiration/expiration ratio.

7. A method according to claim 6, wherein the portion of the system upstream of the gas delivery valve has an associated fluid capacitance volume that is at least three times the volume of the lungs of the subject undergoing evaluation, said method further comprising controllably increasing and decreasing the fluid capacitance volume to stabilize the pressure upstream of the gas delivery valve to reduce the fluctuations in pressure between breaths.

8. A method according to claim 7, further comprising triggering a MRI/NMR hyperpolarized gas signal acquisition sequence during a predetermined portion of the ventilation cycle when hyperpolarized gas is in the subject.

9. A method according to claim 8, wherein the subject is a small animal.

10. A method according to claim 9, wherein the selected breath per minute cycle is about 30 BPM during MRI signal acquisition.

11. A method according to claim 9, further comprising obtaining a NMR/MRI signal having a signal strength and calibrating the NMR/NMR signal strength to the calculated tidal inspiration volume.

12. A method according to claim 11, further comprising monitoring the temperature of the subject.

13. A method according to claim 9, wherein the monitoring steps are carried out during an NMR spectroscopy and/or MRI imaging session.

14. A method according to claim 1, wherein the gas delivery valve is configured to selectively deliver hyperpolarized gas alone, non-polarized gas alone, and/or hyperpolarized gas combined with non-polarized gas, the method further comprising controlling the output of the first mass flow controller and a second mass flow controller to automatically provide desired blends of selected ventilation gases to the subject during non-polarized gas ventilation.

15. A method according to claim 1, wherein the hyperpolarized gas comprises hyperpolarized $^{129}$Xe.

16. A method according to claim 1, wherein the hyperpolarized gas comprises hyperpolarized $^3$He.

17. A method according to claim 1, wherein the gas delivery valve is configured to provide ventilation breath cycles of at least: (a) hyperpolarized gas inhale; (b) non-polarized gas inhale; (c) a combination of hyperpolarized gas and gas non-polarized gas inhale; (d) exhale; (e) partial exhale and hold; (f) hyperpolarized gas inhale and hold; (g) non-polarized gas inhale and hold; and (h) a combination of hyperpolarized gas and gas non-polarized gas inhale and hold.

18. A method according to claim 17, wherein the gas delivery valve receives exhaust gas from the subject and vents the exhaust gas from the gas delivery valve.

19. A method according to claim 1, wherein the tidal volume determination is carried out by subtracting a known fixed calibration volume from the total determined tidal volume.

20. A method according to claim 19, wherein the tidal volume is calculated using the relationship expressed by equation (1):

$$\text{flow rate/frequency} = \text{volume exhausted per cycle} \qquad (1)$$

where "flow rate" is the flow rate of the mass flow controller when the first pressure is substantially constant and frequency is a selected breath per minute rate.

21. A method according to claim 1, wherein the gas delivery valve comprises a plurality of gas actuation valves for actuating selectable gas output flow paths therein.

22. A method according to claim 1, further comprising generating an estimated incremental decrease or increase of output flow rate that can provide a substantially constant first pressure based on the selected breath per minute rate and an estimated delivered volume capacity associated with the type of animal undergoing analysis and adjusting the mass flow controller using the generated value.

23. A method according to claim 1, further comprising generating a computer program library of a priori values of predicted animal volumetric characteristics and/or animal volumetric changes at a plurality of different peak inspiration pressures.

24. A ventilator system having a ventilation flow path for ventilating a subject, comprising:
a gas delivery valve configured to selectively dispense a plurality of different gases to a subject;
a mass flow controller disposed upstream of the gas delivery valve;
a first polarized gas source in fluid communication with the gas delivery valve;
a second gas source in fluid communication with the gas delivery valve;
a first pressure sensor located upstream of the gas delivery valve;
a second pressure sensor located downstream of the gas delivery valve; and
a manifold line having a fluidic tunable capacitance disposed upstream of the gas delivery valve, wherein the fluidic capacitance has a volume that is at least about ten times greater than the volume of the lungs of the subject.

25. A ventilator system according to claim 24, further comprising at least one fixed volume reservoir that is configured to selectively engage the manifold to adjust the fluidic capacitance responsive to pressure measurements obtained by the first and second pressure sensors.

26. A ventilator system according to claim 24, further comprising a syringe with a quantity of fluid therein, the syringe being in communication with the manifold line and configured to selectively add or remove fluid from the manifold.

27. A ventilator system according to claim 24, further comprising a second mass flow controller, wherein the first and second mass flow controllers are used to automatically provide desired blends of selected ventilation gases to the subject.

* * * * *